(12) United States Patent
Flynn et al.

(10) Patent No.: US 9,758,516 B2
(45) Date of Patent: Sep. 12, 2017

(54) CRYSTALLINE FORM OF AN ANXIOLYTIC COMPOUND

(71) Applicant: Bionomics Limited, Thebarton, South Australia (AU)

(72) Inventors: Bernard Luke Flynn, Donvale (AU); Dharam Paul, Flinders Park (AU); Andrew John Harvey, Goodwood (AU)

(73) Assignee: BIONOMICS LIMITED, Thebarton (AU)

( * ) Notice: Subject to any disclaimer, the term of this patent is extended or adjusted under 35 U.S.C. 154(b) by 0 days.

(21) Appl. No.: 14/776,595

(22) PCT Filed: May 14, 2013

(86) PCT No.: PCT/AU2013/000497
§ 371 (c)(1),
(2) Date: Sep. 14, 2015

(87) PCT Pub. No.: WO2014/138772
PCT Pub. Date: Sep. 18, 2014

(65) Prior Publication Data
US 2016/0039810 A1    Feb. 11, 2016

Related U.S. Application Data

(60) Provisional application No. 61/787,436, filed on Mar. 15, 2013.

(30) Foreign Application Priority Data

Apr. 12, 2013    (AU) ................................ 2013204159

(51) Int. Cl.
*C07D 471/04*    (2006.01)

(52) U.S. Cl.
CPC ........ *C07D 471/04* (2013.01); *C07B 2200/13* (2013.01)

(58) Field of Classification Search
None
See application file for complete search history.

(56) References Cited

U.S. PATENT DOCUMENTS 8,293,737 B2    10/2012    Baell et al.

FOREIGN PATENT DOCUMENTS

WO    WO 2012/116410 A1    9/2012
WO    WO 2012/151640 A1    11/2012

OTHER PUBLICATIONS

Hilfiker, R. et al. 2006 "Relevance of Solid-state Properties for Pharmaceutical Products" in *Polymorphism in the Pharmaceutical Industry*; Rolf Hilfiker ed., Chapter 1 (pp. 1-19).

*Primary Examiner* — Samantha Shterengarts
(74) *Attorney, Agent, or Firm* — Knobbe, Martens, Olson & Bear, LLP

(57) ABSTRACT

A crystalline Form B of compound 1 can be used in pharmaceutically compositions. The pharmaceutical compositions can be used in methods of treating a disease (e.g., a disease of the central nervous system).

35 Claims, 10 Drawing Sheets

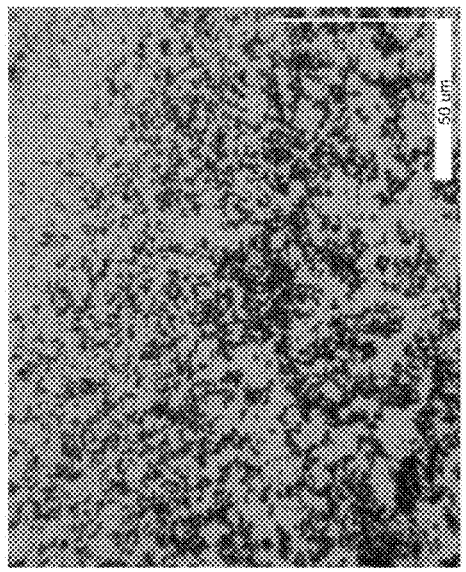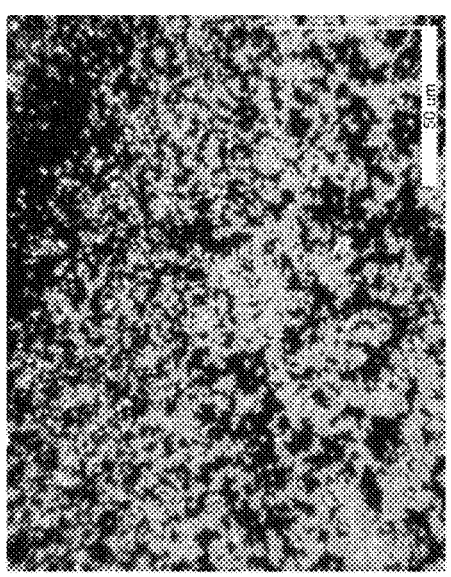
Figures 7A-B

CRYSTALLINE FORM OF AN ANXIOLYTIC COMPOUND

FIELD OF THE INVENTION

The present invention relates generally to a crystalline form of an anxiolytic compound and methods and uses of the crystalline form in therapy and to methods for preparing the crystalline form.

BACKGROUND OF THE INVENTION

Polymorphism denotes the existence of more than one crystal structure of a chemical entity. For any specific chemical entity it is not readily predictable that it will exhibit polymorphism. In the instance when the chemical entity is a drug, the ability of the chemical entity to exist in more than one crystal form can have a profound effect on the shelf life, solubility, formulation properties, and/or processing properties of the drug. Furthermore, the biological action of the drug can be affected by the polymorphism. Different crystalline forms can possess varying rates of uptake in the body, leading to lower or higher biological activity than required. An undesired polymorph may even show toxicity. Therefore the occurrence of an unknown polymorphic form during manufacture and processing of a drug can have a profound impact.

It is therefore important to be able to understand and control polymorphism. Predicting any possible polymorphs for a drug can diminish the possibility of contamination during a drug's manufacture or storage by other polymorphic forms.

Also, understanding which crystal structures are possible in some cases allows researchers to maximize the desired properties of a compound, such as solubility, formulation properties, processing properties, and shelf life. Understanding these factors early in the development of a new drug may mean a more active, more stable, or more cheaply manufactured drug.

SUMMARY OF THE INVENTION

U.S. Pat. No. 8,293,737, the entirety of which is incorporated herein by reference, describes certain 1,8-naphthyridin-4(1H)-one compounds which are useful as anxiolytic agents. Such compounds include 1-ethyl-6-(indan-2-ylamino)-3-(morpholine-4-carbonyl)-1,8-naphthyridin-4-one (compound 1).

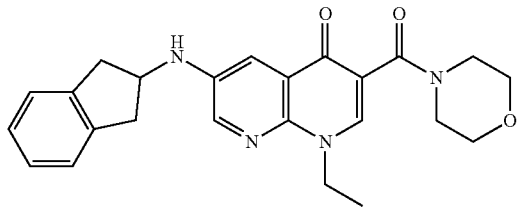

1

Compound 1 possesses anxiolytic activity without sedative side effects and therefore represents an attractive alternative to the 1,4-benzodiazepine class of anxiolytics such as diazepam.

A polymorph of compound 1 has been discovered and named Form B, and compositions thereof, are useful as therapeutics and in the preparation of pharmaceutical compositions and exhibit desirable characteristics for such purposes. In general, Form B, and pharmaceutical compositions thereof, are useful for treating or lessening the severity of a variety of diseases or disorders described herein (e.g., an anxiety disorder). Form B is a stable crystalline hemihydrate form of compound 1. Form B can be characterized using various techniques as described herein including, but not limited to, x-ray powder diffraction, Raman spectroscopy, differential scanning calorimetry, dynamic vapor sorption, and thermogravimetric Fourier-transfor infrared thermogram.

Also provided herein is a pharmaceutical composition comprising Form B of compound 1 and optionally an additional ingredient selected from pharmaceutically acceptable carriers, diluents, and excipients.

Also provided herein are methods of treating various diseases, disorders, or conditions comprising administering to a subject Form B of compound 1, or a pharmaceutical composition thereof as described herein.

Also provided herein are uses of Form B of compound 1, or a pharmaceutical composition thereof as described herein for treating various diseases, disorders, or conditions.

Also provided herein are uses of Form B of compound 1, or a pharmaceutical composition thereof as described herein in the manufacture of a medicament for treating various diseases, disorders, or conditions.

DEFINITIONS

The term "solvate" refers to forms of a compound (e.g., compound 1) that are associated with a solvent, usually by a solvolysis reaction. This physical association may include hydrogen bonding. Conventional solvents include water, methanol, ethanol, acetic acid, DMSO, THF, diethyl ether, and the like. In certain embodiments, solvates are formed using Class 3 solvents. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). A compound may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate," refers to a compound (e.g., compound 1) which is associated with water. Typically, the number of the water molecules contained in a hydrate of a compound is in a definite ratio to the number of the compound molecules in the hydrate. Hydrates include both stoichiometric hydrates and non-stoichiometric hydrates. Therefore, a hydrate of a compound may be represented, for example, by the general formula $R \cdot xH_2O$, wherein R is the compound and wherein x is a number greater than 0. A given compound may form more than one type of hydrates, including, e.g., monohydrates (stoichiometric, x is 1), lower hydrates (non-stoichiometric, x is a number greater than 0 and smaller than 1, e.g., hemihydrates ($R \cdot 0.5H_2O$)), and polyhydrates (non-stoichiometric, x is a number greater than 1, e.g., dihydrates ($R \cdot 2H_2O$) and hexahydrates ($R \cdot 6H_2O$)).

It is also to be understood that compounds that have the same molecular formula but differ in the nature or sequence of bonding of their atoms or the arrangement of their atoms in space are termed "isomers".

The term "polymorphs" refers to a crystalline form of a compound (e.g., compound 1), or a hydrate or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystalline form to dominate. Various polymorphs of a compound, or a hydrate or solvate thereof, can be prepared by crystallization under different conditions.

As used herein, the term "impurity" refers to extraneous matter included in a compound (e.g., Form B of compound 1). Extraneous matter includes one or more substances that are different from the compound. In certain embodiments, the extraneous matter is undesired extraneous matter. For example, when an anhydrous compound is desired, the solvent (e.g., water) included in the compound is an impurity. When a crystalline compound is desired, an amorphous form of the compound included in the compound is an impurity. When certain polymorph of a compound is desired, a different polymorph of the compound included in the compound is an impurity. The term "substantially free of impurities" means that a compound (e.g., Form B of compound 1), contains no significant amount of extraneous matter (e.g., undesired extraneous matter). What amount of the extraneous matter constitutes a significant amount depends on the subject matter and is understood in the art. In certain embodiments, about 1 wt %, about 2 wt %, about 3 wt %, about 5 wt %, about 7 wt %, or about 10 wt % of extraneous matter in a compound is a significant amount of extraneous matter.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is fish.

The terms "administer," "administering," or "administration," as used herein, refers to implanting, absorbing, ingesting, injecting, inhaling, or otherwise introducing a compound (e.g., Form B of compound 1) or pharmaceutical composition thereof, in or on a subject.

As used herein, the terms "in combination" and "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms. Treatment may also be continued after symptoms have resolved, for example, to delay or prevent recurrence.

The terms "prevention," "prevent," and "preventing," as used herein, refer to administering a medicament (e.g., Form B of compound 1 or a pharmaceutical composition thereof) beforehand to avert or forestall the appearance of one or more symptoms of a disease or disorder. The person of ordinary skill in the medical art recognizes that the terms "prevention," "prevent," and "preventing" are not absolute terms. In the medical art these terms are understood to refer to the prophylactic administration of a medicament to substantially diminish the likelihood or seriousness of a condition, or symptom of the condition, and this is the sense intended in this disclosure.

As used herein, the terms "condition," "disease," and "disorder" are used interchangeably.

An "effective amount" of a compound described herein refers to an amount sufficient to elicit the desired biological response, e.g., treating a condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating an anxiety disorder, an effective amount of an inventive compound may provide a therapeutic and/or prophylactic benefit in the treatment and/or prevention of the anxiety disorder or to delay or minimize one or more symptoms associated with the anxiety disorder.

A "therapeutically effective amount" of a compound described herein is an amount sufficient to provide a therapeutic benefit in the treatment of a condition (e.g., an anxiety disorder) or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound described herein is an amount sufficient to prevent a condition (e.g., an anxiety disorder), or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neurite" refers to any projection from the cell body of a neuron. This projection can be either an axon or a dendrite. Neurites are often packed with microtubule bundles, the growth of which is stimulated by Nerve Growth Factor (NGF), as well as tau proteins, MAP1, and MAP2. The neural cell adhesion molecule N-CAM simultaneously combines with another N-CAM and a fibroblast growth factor receptor to stimulate the tyrosine kinase activity of that receptor to induce the growth of neurites.

A disease "responsive to neurite outgrowth" is a disease, disorder, or condition which may be ameliorated by enhancement of neurite outgrowth. Diseases responsive to neurite outgrowth include neurodegenerative diseases (e.g., multiple sclerosis and a Parkinsonian related disorder) and diseases that involve neural damage that include wound healing, spinal cord injury, and peripheral nerve disorders.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

FIGS. 7A-B depict microscopic images of Form B recorded without (FIG. 7A) and with (FIG. 7B) crossed polarizers. Compound 1 appears dark in the left image and bright in the right image.

DETAILED DESCRIPTION OF CERTAIN EMBODIMENTS

Figure 1:
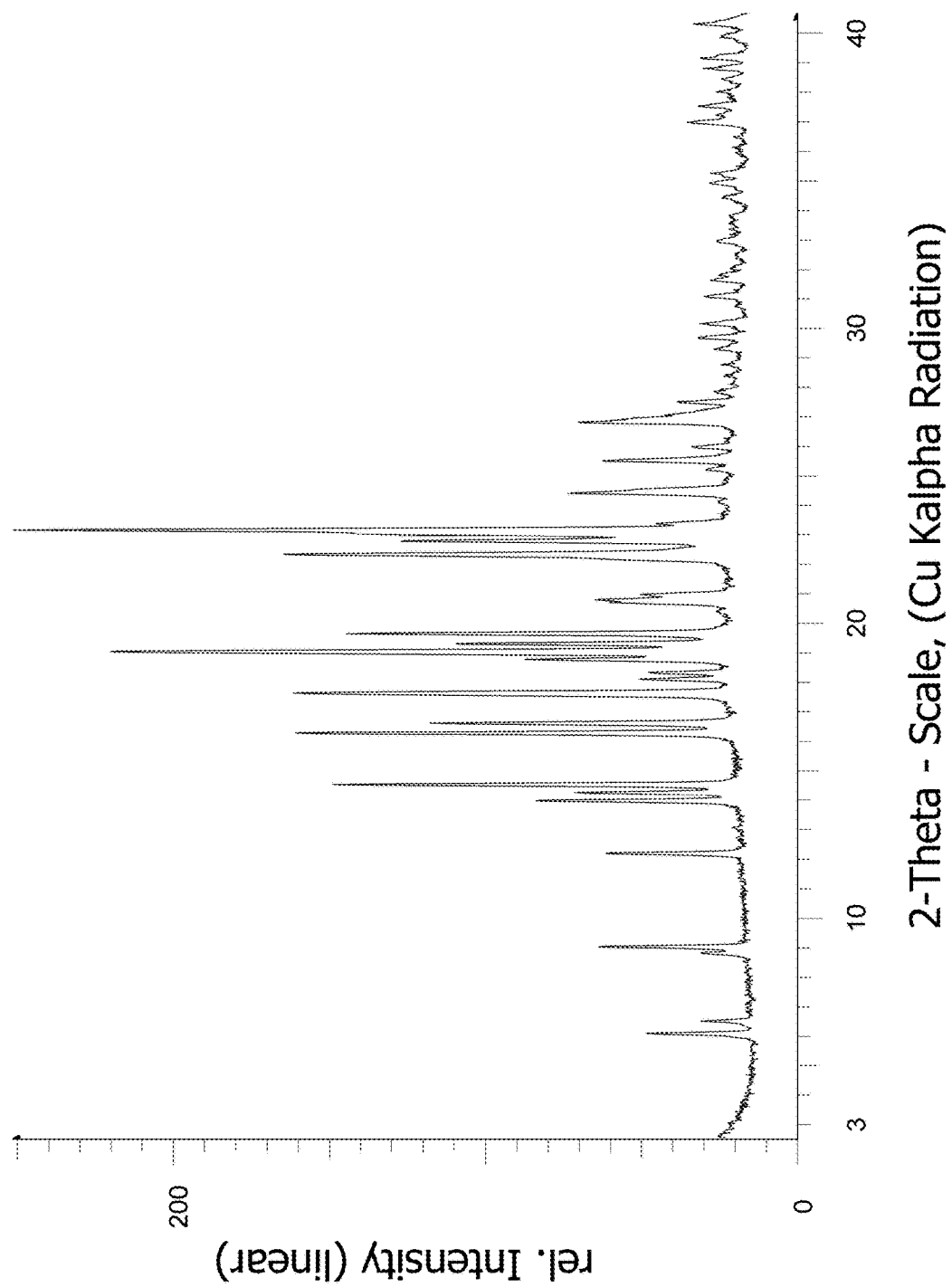
FIG. 1 depicts an X-Ray Powder Diffraction (XRPD) pattern of Form B.

Compound 1 (1-ethyl-6-(indan-2-ylamino)-3-(morpholine-4-carbonyl)-1,8-naphthyridin-4-one) has been reported to elicit an anxiolytic effect. Compound 1 has shown significant potential for the treatment of a variety of disorders of the central nervous system (CNS), such as anxiety disorders. See, e.g., U.S. Pat. No. 8,293,737.

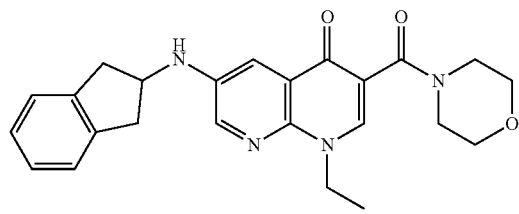

1

Solid Form

In some embodiments, it would be desirable to provide a crystalline polymorph of compound 1 that, as compared to the amorphous compound 1, imparts improved physical characteristics such as stability and/or ease of formulation. Accordingly, provided herein is a crystalline form (denoted Form B) of compound 1. Form B is a hemihydrate of compound 1. Form B is stable upon drying, and other solvates of compound 1 were less stable upon drying. For example, solvates of methanol, ethanol, isopropanol, tetrahydrofuran (THF), and dioxane either changed from or showed a reduction in crystallinity upon drying. In some embodiments, Form B has a water content of about 2.0 wt %. Form B is substantially non-hygroscopic. In contrast, anhydrous forms of compound 1 were found to show indications of hygroscopicity. Form B was also found to be more stable than an anhydrous form of compound 1. In a competitive slurry experiment there was a tendency for the anhydrous form to convert to Form B.

In some embodiments, Form B is substantially free of impurities. In some embodiments, Form B is 99% free of impurities. In some embodiments, Form B is 97% free of impurities. In some embodiments, Form B is 95% free of impurities. In some embodiments, Form B is 92% free of impurities. In some embodiments, Form B is 90% free of impurities. In certain embodiments, the impurities include extraneous matter, such as a salt forming acid, residual solvents, or any other impurities that may result from the preparation, and/or isolation, of compound 1. In, some embodiments, Form B is substantially free of amorphous compound 1. In some embodiments, Form B is substantially free of another crystalline form of compound 1. In some embodiments, Form B is substantially free of a salt of compound 1. In some embodiments, Form B is substantially free of a non-water solvate of compound 1. In some embodiments, Form B is obtained from mixture of methanol and water.

Different solid forms of a compound typically differ in their physical and chemical properties based on the arrangement of the molecules in the solid form (e.g., the arrangement of the molecule in the crystal lattice). A given substance may give rise to a variety of solid forms, in particular a variety of crystalline forms, wherein each form has different and distinct physical and chemical properties, such as solubility profiles, thermodynamic and chemical stabilities, melting points, Raman spectra, and/or x-ray diffraction peaks.

Form B can be characterized by one or more of the characteristics described herein including, but not limited to, XRPD diffraction pattern and/or peaks, Raman spectrum and/or peaks, DSC thermogram, DVS isotherm, TG-FTIR thermogram, IR spectrum and/or peaks, appearance, melting point, solubility, and stability. In certain embodiments, Form B is characterized by XRPD diffraction pattern and/or peaks and Raman spectrum and/or peaks. In certain embodiments, Form B is characterized by XRPD diffraction pattern and/or peaks, Raman spectrum and/or peaks, and at least one other technique as described herein (e.g., DSC thermogram, DVS isotherm, TG-FTIR thermogram, melting point).

In some embodiments, Form B is characterized by an X-ray powder diffraction pattern substantially similar to the one depicted in FIG. 1. In some embodiments, Form B is characterized in that it has one or more peaks in its X-ray powder diffraction pattern selected from those in Table 1. In some embodiments, Form B is characterized by at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, at least thirty, at least thirty-one, at least thirty-two, at least thirty-three, or at least thirty-four peaks in its X-ray powder diffraction pattern selected from those in Table 1. In some embodiments, Form B of compound 1 is characterized in that it has one or more peaks in its X-ray powder diffraction pattern selected from the strong and very strong peaks in Table 1. In some embodiments, Form B of compound 1 is characterized in that it has all the peaks in its X-ray powder diffraction pattern selected from the strong and very strong peaks in Table 1. In some embodiments, Form B of compound 1 is characterized in that it has one or more peaks in its X-ray powder diffraction pattern selected from the very strong peaks in Table 1. In some embodiments, Form B of compound 1 is characterized in that it has all the peaks in its X-ray powder diffraction pattern selected from the very strong peaks in Table 1. In some embodiments, Form B of compound 1 is characterized in that it has both very strong peaks listed in Table 1 (i.e., 19.02 and 23.16 angle theta-2).

TABLE 1

X-ray powder diffraction pattern.

| Angle 2-Theta ° | d value Angstrom | Intensity (relative) | Intensity % |
|---|---|---|---|
| 6.05 | 14.6 | m | 16 |
| 6.48 | 13.6 | w | 10 |
| 8.78 | 10.1 | w | 11 |
| 9.00 | 9.8 | m | 22 |
| 12.16 | 7.3 | m | 23 |
| 13.94 | 6.3 | s | 31 |
| 14.25 | 6.2 | m | 25 |
| 14.52 | 6.1 | s | 55 |
| 16.27 | 5.45 | s | 60 |
| 16.60 | 5.34 | s | 42 |
| 17.62 | 5.03 | s | 57 |
| 18.09 | 4.90 | m | 18 |
| 18.31 | 4.84 | m | 17 |
| 18.76 | 4.73 | s | 32 |
| 19.02 | 4.66 | vs | 79 |
| 19.29 | 4.60 | s | 43 |
| 19.64 | 4.52 | s | 54 |
| 20.78 | 4.27 | m | 23 |
| 20.95 | 4.24 | m | 17 |
| 22.32 | 3.98 | s | 60 |
| 22.77 | 3.90 | s | 50 |
| 23.02 | 3.86 | s | 53 |
| 23.16 | 3.84 | vs | 100 |
| 23.39 | 3.80 | m | 17 |
| 24.42 | 3.64 | m | 30 |
| 25.53 | 3.49 | m | 25 |
| 25.97 | 3.43 | w | 12 |
| 26.82 | 3.32 | m | 28 |
| 27.51 | 3.24 | w | 14 |
| 29.69 | 3.01 | w | 12 |
| 30.17 | 2.96 | w | 12 |
| 31.10 | 2.87 | w | 11 |
| 31.65 | 2.83 | w | 11 |
| 34.96 | 2.56 | w | 11 |

The terms used in the tables herein have the following meanings: The term "vs" stands for "very strong." The term "s" stands for "strong." The term "m" stands for "medium." The term "w" stands for "weak." The term "vw" stands for "very weak."

In some embodiments, Form B is characterized by one or more peaks in its X-ray powder diffraction pattern selected from those in Table 2. In some embodiments, Form B is characterized by at least one, at least two, at least three, at least four, at least five, at least six, at least seven, at least eight, at least nine, at least ten, at least eleven, at least twelve, or at least thirteen peaks in its X-ray powder diffraction pattern selected from those in Table 2. In some embodiments, the characteristic peaks include at least the two very strong peaks indicated in Table 2. In some embodiments, Form B is characterized by the two very strong peaks indicated in Table 2, and at least one, at least two, at least three, at least four, at least five, at least six, at least seven, at least eight, at least nine, at least ten, at least eleven, at least twelve, or at least thirteen of the other strong peaks in its X-ray powder diffraction pattern selected from those in Table 2.

TABLE 2

Select characteristic peaks from the X-ray powder diffraction pattern.

| Angle 2-Theta ° | d value Angstrom | Intensity (relative) | Intensity % |
|---|---|---|---|
| 13.94 | 6.3 | s | 31 |
| 14.52 | 6.1 | s | 55 |
| 16.27 | 5.45 | s | 60 |
| 16.60 | 5.34 | s | 42 |
| 17.62 | 5.03 | s | 57 |
| 18.76 | 4.73 | s | 32 |
| 19.02 | 4.66 | vs | 79 |
| 19.29 | 4.60 | s | 43 |
| 19.64 | 4.52 | s | 54 |
| 22.32 | 3.98 | s | 60 |
| 22.77 | 3.90 | s | 50 |
| 23.02 | 3.86 | s | 53 |
| 23.16 | 3.84 | vs | 100 |

For instance, in one embodiment Form B is characterised by the 6 peaks (from Table 2) with the Angle 2-Theta° values of 13.94, 14.52, 16.27, 19.02, 22.32, and 23.16.

Figure 2:
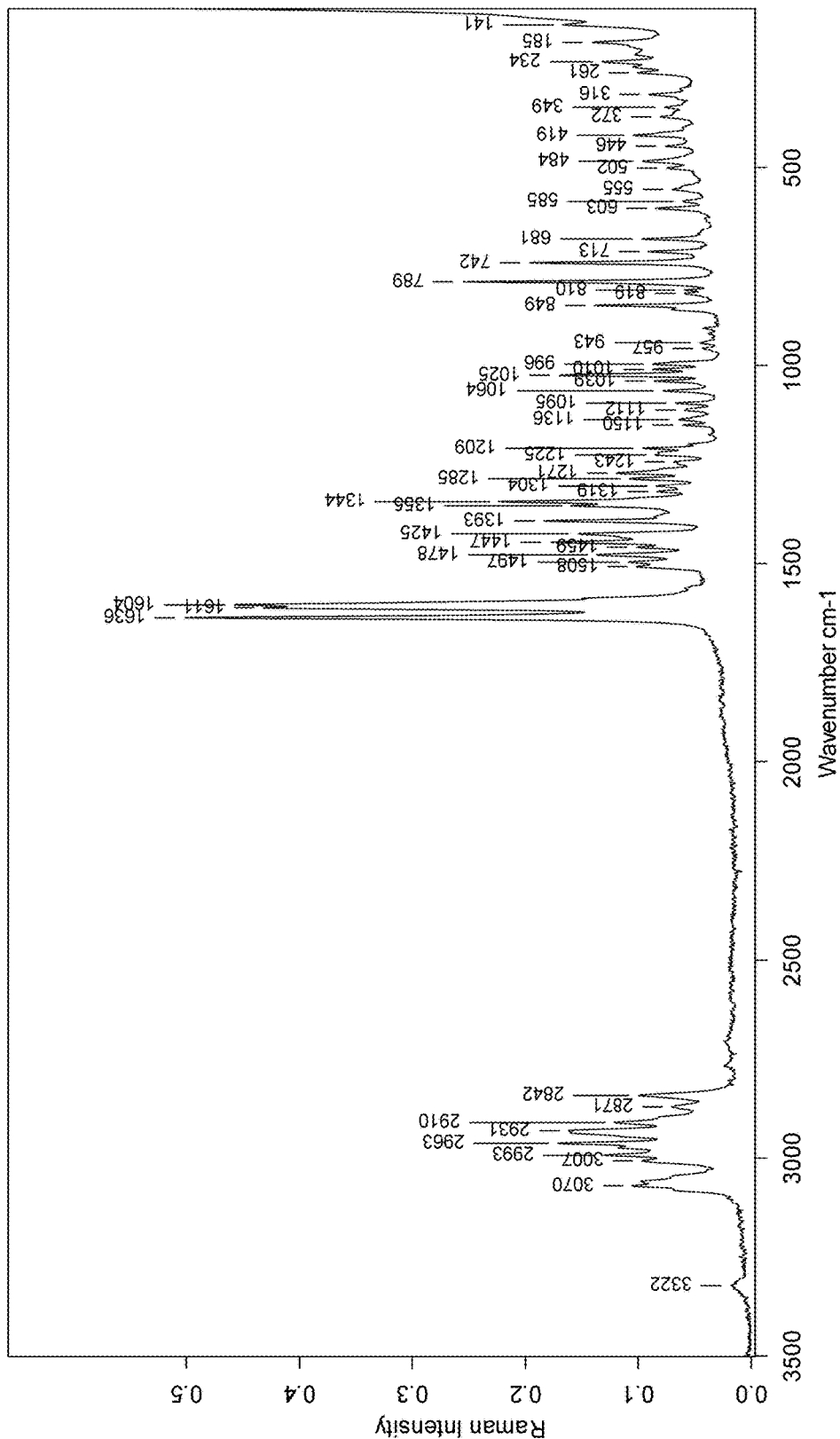
FIG. 2 depicts a Fourier-Transform Raman (FT-Raman) spectrum of Form B.

In some embodiments, Form B is characterized by a Raman spectrum substantially similar to the one depicted in FIG. 2. In some embodiments, Form B is characterized by one or more peaks in its Raman spectrum selected from those in Table 3. In some embodiments, Form B is characterized by at least one, at least two, at least three, at least four, at least five, at least six, at least seven, at least eight, at least nine, at least ten, at least fifteen, at least twenty, at least thirty, at least forty, at least fifty, or at least sixty peaks in its Raman spectrum selected from those in Table 3.

In some embodiments, Form B is characterized by (1) a Raman spectrum substantially similar to the one depicted in FIG. 2 and (2) an X-ray powder diffraction pattern substantially similar to the one depicted in FIG. 1. In some embodiments, Form B is characterized by (1) a Raman spectrum substantially similar to the one depicted in FIG. 2 and (2) one or more peaks in its X-ray powder diffraction pattern selected from those in Table 1. In some embodiments, Form B is characterized by (1) a Raman spectrum substantially similar to the one depicted in FIG. 2; and (2) one or more peaks in its X-ray powder diffraction pattern selected from those in Table 2. In some embodiments, Form B is characterized by (1) a Raman spectrum substantially similar to the one depicted in FIG. 2; and (2) the two very strong peaks indicated in Table 2 and at least one, at least two, at least three, at least four, at least five, at least six, at least seven, at least eight, at least nine, at least ten, or at least eleven of the other strong peaks in its X-ray powder diffraction pattern selected from those in Table 2. In some embodiments, Form B is characterized by (1) at least one, at least two, at least three, at least four, at least five, at least six, at least seven, at least eight, at least nine, at least ten, at least fifteen, at least twenty, at least thirty, at least forty, at least fifty, or at least sixty peaks in its Raman spectrum selected from those in Table 3; and (2) one or more peaks in its X-ray powder diffraction pattern selected from those in Table 2. In some embodiments, Form B is characterized by (1) at least one, at least two, at least three, at least four, at least five, at least six, at least seven, at least eight, at least nine, at least ten, at least fifteen, at least twenty, at least thirty, at least forty, at least fifty, or at least sixty peaks in its Raman spectrum selected from those in Table 3; and (2) the two very strong peaks indicated in Table 2 and at least one, at least two, at least three, at least four, at least five, at least six, at least seven, at least eight, at least nine, at least ten, or at least eleven of the other strong peaks in its X-ray powder diffraction pattern selected from those in Table 2.

TABLE 3

Raman spectrum.

| Wavenumber (cm$^{-1}$) | Absolute Intensity | Normalized Intensity (%) |
|---|---|---|
| 3322 | 0.018 | 3.6 |
| 3070 | 0.105 | 20.9 |
| 3007 | 0.097 | 19.3 |
| 2993 | 0.131 | 26.1 |
| 2963 | 0.171 | 34.1 |
| 2931 | 0.162 | 32.3 |
| 2910 | 0.121 | 24.1 |
| 2871 | 0.070 | 13.9 |
| 2842 | 0.100 | 19.9 |
| 1636 | 0.502 | 100.0 |
| 1611 | 0.432 | 86.1 |
| 1604 | 0.457 | 91.0 |
| 1508 | 0.101 | 20.1 |
| 1497 | 0.108 | 21.5 |
| 1478 | 0.137 | 27.3 |
| 1459 | 0.101 | 20.1 |
| 1446 | 0.178 | 35.5 |
| 1425 | 0.153 | 30.5 |
| 1393 | 0.184 | 36.7 |
| 1355 | 0.160 | 31.9 |
| 1344 | 0.224 | 44.6 |
| 1319 | 0.083 | 16.5 |
| 1304 | 0.084 | 16.7 |
| 1285 | 0.107 | 21.3 |
| 1271 | 0.119 | 23.7 |
| 1243 | 0.068 | 13.5 |
| 1225 | 0.085 | 16.9 |
| 1208 | 0.096 | 19.1 |
| 1150 | 0.061 | 12.2 |
| 1136 | 0.064 | 12.7 |
| 1112 | 0.058 | 11.6 |
| 1095 | 0.067 | 13.3 |
| 1064 | 0.078 | 15.5 |
| 1039 | 0.086 | 17.1 |
| 1025 | 0.170 | 33.9 |
| 1010 | 0.087 | 17.3 |
| 996 | 0.087 | 17.3 |
| 957 | 0.043 | 8.6 |
| 943 | 0.045 | 9.0 |
| 849 | 0.139 | 27.7 |
| 819 | 0.059 | 11.8 |
| 810 | 0.059 | 11.8 |
| 789 | 0.255 | 50.8 |
| 741 | 0.196 | 39.0 |
| 713 | 0.091 | 18.1 |
| 681 | 0.096 | 19.1 |
| 603 | 0.084 | 16.7 |
| 585 | 0.060 | 12.0 |
| 555 | 0.070 | 13.9 |
| 501 | 0.075 | 14.9 |
| 484 | 0.096 | 19.1 |
| 446 | 0.076 | 15.1 |

TABLE 3-continued

Raman spectrum.

| Wavenumber (cm$^{-1}$) | Absolute Intensity | Normalized Intensity (%) |
|---|---|---|
| 419 | 0.104 | 20.7 |
| 372 | 0.080 | 15.9 |
| 349 | 0.076 | 15.1 |
| 316 | 0.090 | 17.9 |
| 261 | 0.100 | 19.9 |
| 234 | 0.132 | 26.3 |
| 185 | 0.141 | 28.1 |
| 141 | 0.167 | 33.3 |

In some embodiments, Form B is characterized by one or more peaks in its Raman spectrum selected from those in Table 4. In some embodiments, Form B is characterized by at least one, at least two, at least three, at least four, at least five, at least six, at least seven, at least eight, at least nine, at least ten, or at least eleven peaks in its Raman spectrum selected from those in Table 4. In some embodiments, Form B is characterized by (1) one or more peaks in its Raman spectrum selected from those in Table 4; and (2) an X-ray powder diffraction pattern substantially similar to the one depicted in FIG. 1. In some embodiments, Form B is characterized by (1) one or more peaks in its Raman spectrum selected from those in Table 4; and (2) one or more peaks in its X-ray powder diffraction pattern selected from those in Table 1. In some embodiments, Form B is characterized by (1) one or more peaks in its Raman spectrum selected from those in Table 4; and (2) one or more peaks in its X-ray powder diffraction pattern selected from those in Table 2. In some embodiments, Form B is characterized by (1) at least one, at least two, at least three, at least four, at least five, at least six, at least seven, at least eight, at least nine, at least ten, or at least eleven peaks in its Raman spectrum selected from those in Table 4; and (2) one or more peaks in its X-ray powder diffraction pattern selected from those in Table 2.

TABLE 4

Select characteristic peaks from the Raman spectrum.

| Wavenumber (cm$^{-1}$) | Absolute Intensity | Normalized Intensity (%) |
|---|---|---|
| 1636 | 0.502 | 100.0 |
| 1611 | 0.432 | 86.1 |
| 1604 | 0.457 | 91.0 |
| 1446 | 0.178 | 35.5 |
| 1425 | 0.153 | 30.5 |
| 1393 | 0.184 | 36.7 |
| 1355 | 0.160 | 31.9 |
| 1344 | 0.224 | 44.6 |
| 1025 | 0.170 | 33.9 |
| 789 | 0.255 | 50.8 |
| 741 | 0.196 | 39.0 |

For instance, in some embodiments Form B is characterised by the 8 peaks (from Table 4) with the following wavenumbers (cm$^{-1}$) 1636, 1604, 1446, 1425, 1393, 1355, 1025, and 741.

Figure 10:
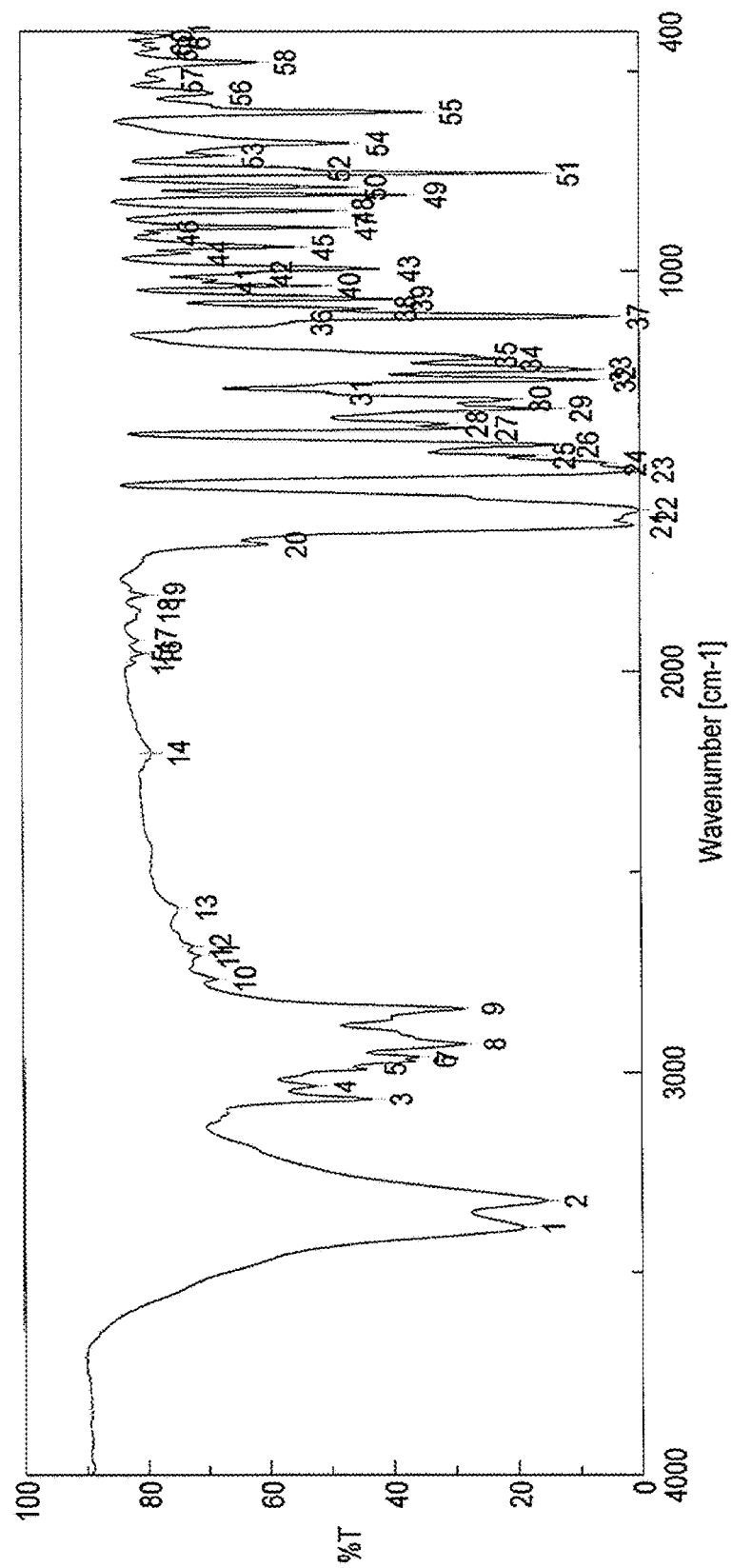
FIG. 10 depicts an infrared (IR) spectrum of Form B.

In some embodiments, Form B is characterized by an IR spectrum substantially similar to the one depicted in FIG. 10. In some embodiments, Form B is characterized by one or more peaks in its IR spectrum selected from those in Table 9.

TABLE 9

IR spectrum.

| No. | Position | Intensity | No. | Position | Intensity | No. | Position | Intensity |
|---|---|---|---|---|---|---|---|---|
| 1 | 3389.28 | 18.8803 | 2 | 3321.78 | 15.2998 | 3 | 3066.26 | 43.3187 |
| 4 | 3033.48 | 52.327 | 5 | 2991.05 | 44.2454 | 6 | 2970.8 | 36.2048 |
| 7 | 2960.2 | 35.8651 | 8 | 2928.38 | 28.2099 | 9 | 2839.67 | 28.5464 |
| 10 | 2765.42 | 68.3886 | 11 | 2707.57 | 71.199 | 12 | 2684.43 | 72.4374 |
| 13 | 2588.97 | 74.7507 | 14 | 2204.24 | 79.2123 | 15 | 1976.68 | 81.6905 |
| 16 | 1954.5 | 80.4172 | 17 | 1921.72 | 81.2251 | 18 | 1847.47 | 80.7596 |
| 19 | 1807.94 | 79.7842 | 20 | 1680.66 | 59.904 | 21 | 1632.45 | 1.12286 |
| 22 | 1593.88 | 0.229197 | 23 | 1493.6 | 0.785332 | 24 | 1476.24 | 5.24501 |
| 25 | 1458.89 | 16.6916 | 26 | 1431.89 | 12.9634 | 27 | 1390.42 | 25.9737 |
| 28 | 1379.82 | 30.7322 | 29 | 1341.25 | 14.0312 | 30 | 1318.11 | 20.5376 |
| 31 | 1301.72 | 49.2933 | 32 | 1269.9 | 6.91712 | 33 | 1244.83 | 7.5622 |
| 34 | 1216.86 | 21.9545 | 35 | 1209.15 | 26.0253 | 36 | 1128.15 | 55.6498 |
| 37 | 1113.69 | 4.73713 | 38 | 1093.44 | 42.0985 | 39 | 1068.37 | 39.536 |
| 40 | 1036.55 | 51.1775 | 41 | 1023.05 | 68.0011 | 42 | 1005.7 | 62.1369 |
| 43 | 994.125 | 41.5655 | 44 | 955.555 | 72.4243 | 45 | 940.128 | 55.4283 |
| 46 | 905.415 | 77.3957 | 47 | 889.987 | 48.5083 | 48 | 848.525 | 48.9604 |
| 49 | 808.992 | 37.3274 | 50 | 789.707 | 46.8949 | 51 | 754.995 | 16.0235 |
| 52 | 743.424 | 52.7696 | 53 | 710.64 | 66.7717 | 54 | 679.785 | 46.5898 |
| 55 | 601.682 | 34.7989 | 56 | 554.434 | 68.6904 | 57 | 521.65 | 76.6701 |
| 58 | 477.296 | 61.4961 | 59 | 442.583 | 77.4332 | 60 | 428.12 | 78.2972 |
| 61 | 410.763 | 75.3479 | | | | | | |

In some embodiments Form B is characterised by the 5 peaks (from Table 9) with the following wavenumbers (cm$^{-1}$) 1632.45, 1593.88, 1244.83, 754.995, and 601.682.

In some embodiments, Form B is characterized by (1) an XRPD patterns having peaks shown in Table 2a, (2) Raman spectrum with characteristic peaks shown in the Table 3a, (3) IR spectrum with characteristic peaks shown Table 9a, and (4) a DSC thermogram with an endotherm having a peak temperature ($T_{max}$) of about 176° C.

TABLE 2A

Select characteristic peaks the XRPD spectrum of Form B

| Angle 2-Theta ° | d value Angstrom | Intensity (relative) | Intensity % |
|---|---|---|---|
| 13.94 | 6.3 | s | 31 |
| 23.16 | 3.84 | vs | 100 |

TABLE 3A

Select characteristic peaks from the Raman spectrum of form B.

| Wavenumber (cm$^{-1}$) | Absolute Intensity | Normalized Intensity (%) |
|---|---|---|
| 1636 | 0.502 | 100.0 |
| 1604 | 0.457 | 91.0 |
| 741 | 0.196 | 39.0 |

TABLE 9A

Select characteristic Peaks from the IR Spectrum of form B

| Wavenumber Cm$^{-1}$ | % T |
|---|---|
| 1632.45 | 1.12286 |
| 1593.88 | 0.229197 |
| 1244.83 | 7.5622 |
| 754.995 | 16.0235 |

In some embodiments, Form B is characterized by (1) an XRPD patterns having peaks shown in Table 2b, (2) Raman spectrum with characteristic peaks shown in the Table 3 b, (3) IR spectrum with characteristic peaks shown Table 9b, and (4) a DSC thermogram with an endotherm having a peak temperature ($T_{max}$) of about 176° C.

TABLE 2B

Select characteristic peaks the XRPD spectrum of Form B

| Angle 2-Theta ° | d value Angstrom | Intensity (relative) | Intensity % |
|---|---|---|---|
| 13.94 | 6.3 | s | 31 |
| 19.02 | 4.66 | vs | 79 |
| 23.16 | 3.84 | vs | 100 |

TABLE 3B

Select characteristic peaks from the Raman spectrum of form B.

| Wavenumber (cm$^{-1}$) | Absolute Intensity | Normalized Intensity (%) |
|---|---|---|
| 1636 | 0.502 | 100.0 |
| 1604 | 0.457 | 91.0 |
| 1025 | 0.170 | 33.9 |
| 741 | 0.196 | 39.0 |

TABLE 9B

Select characteristic Peaks from the IR Spectrum of form B

| Wavenumber (cm$^{-1}$) | % T |
|---|---|
| 1632.45 | 1.12286 |
| 1593.88 | 0.229197 |
| 1244.83 | 7.5622 |
| 754.995 | 16.0235 |
| 601.682 | 34.7989 |

In some embodiments, Form B is characterized by (1) an XRPD patterns having peaks shown in Table 2c, (3) IR spectrum with characteristic peaks shown Table 9c, and (3) a DSC thermogram with an endotherm having a peak temperature ($T_{max}$) of about 176° C.

TABLE 2C

Select characteristic peaks the XRPD spectrum of Form B

| Angle 2-Theta ° | d value Angstrom | Intensity (relative) | Intensity % |
|---|---|---|---|
| 13.94 | 6.3 | s | 31 |
| 19.02 | 4.66 | vs | 79 |
| 23.16 | 3.84 | vs | 100 |

TABLE 9C

Select characteristic Peaks from the IR Spectrum of form B

| Wavenumber (cm$^{-1}$) | % T |
|---|---|
| 1632.45 | 1.12286 |
| 1593.88 | 0.229197 |
| 754.995 | 16.0235 |
| 601.682 | 34.7989 |

In some embodiments, Form B is characterised by the following:
(i) Characteristic peaks from the XRPD spectrum of Form B

| Angle 2-Theta ° | d value Angstrom | Intensity (relative) | Intensity (%) |
|---|---|---|---|
| 13.94 | 6.3 | s | 31 |
| 14.52 | 6.1 | s | 55 |
| 16.27 | 5.45 | s | 60 |
| 19.02 | 4.66 | vs | 79 |
| 22.32 | 3.98 | s | 60 |
| 23.16 | 3.84 | vs | 100 | and
(ii) Characteristic peaks from the Raman spectrum of Form B.

| Wavenumber (cm$^{-1}$) | Absolute Intensity | Normalized Intensity (%) |
|---|---|---|
| 1636 | 0.502 | 100.0 |
| 1604 | 0.457 | 91.0 |
| 1446 | 0.178 | 35.5 |
| 1425 | 0.153 | 30.5 |
| 1393 | 0.184 | 36.7 |
| 1355 | 0.160 | 31.9 |
| 1025 | 0.170 | 33.9 |
| 741 | 0.196 | 39.0 | and
(iii) Characteristic Peaks from the IR Spectrum of Form B

| Wavenumber (cm$^{-1}$) | % T |
|---|---|
| 1632.45 | 1.12286 |
| 1593.88 | 0.229197 |
| 1244.83 | 7.5622 |
| 754.995 | 16.0235 |
| 601.682 | 34.7989 | and
(iv) a DSC thermogram with an endotherm having a peak temperature ($T_{max}$) of about 176° C.

Figure 3:
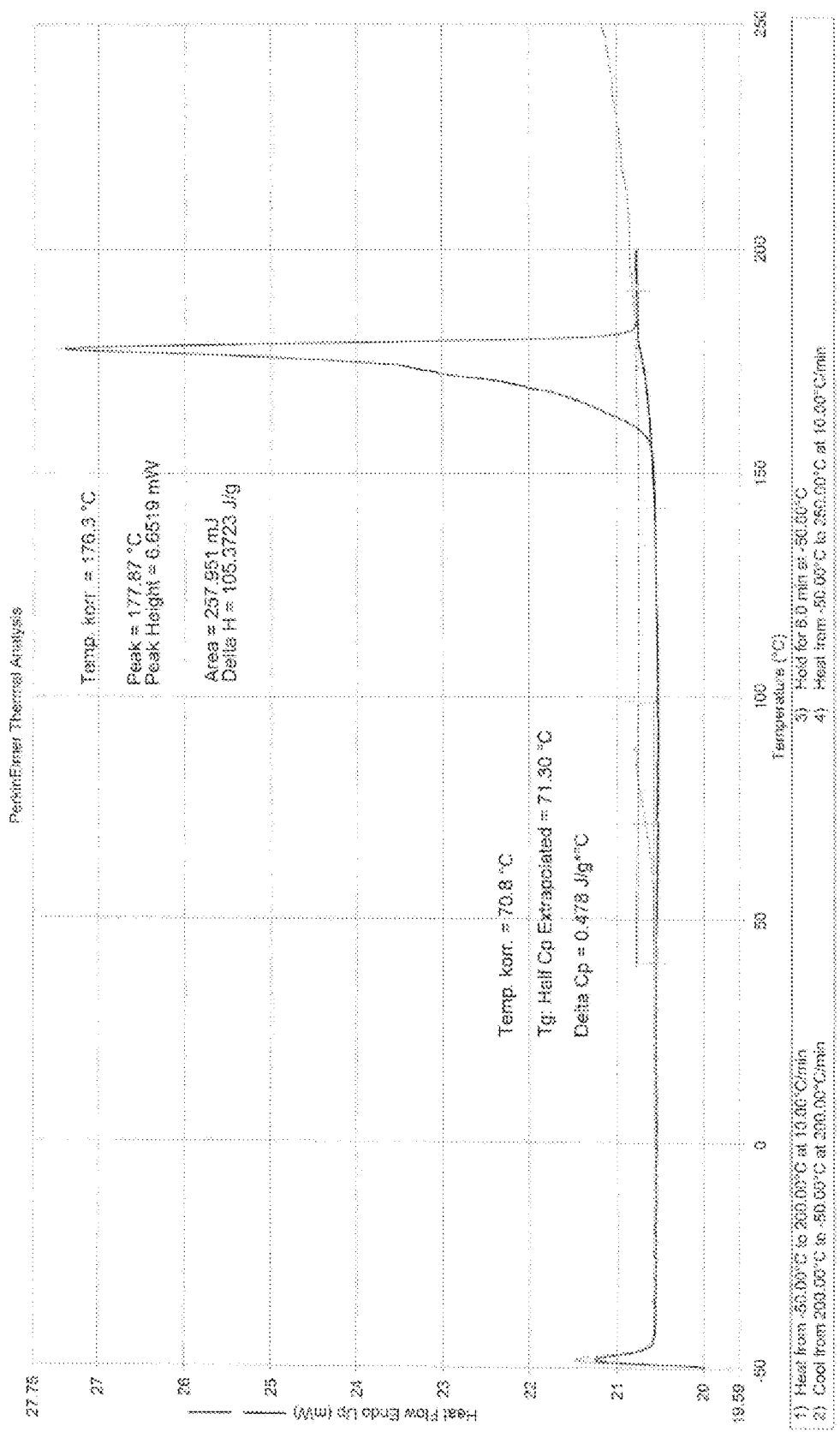
FIG. 3 depicts a Differential Scanning calorimetry (DSC) thermogram of Form B.

In some embodiments, Form B has a DSC thermogram substantially similar to the one depicted in FIG. 3. In some embodiments, Form B is characterized in that it has a DSC thermogram with an endotherm having a peak temperature ($T_{max}$) of about 176° C. In some embodiments, Form B is characterized in that it has a DSC thermogram with a ΔH of about 105 J/g. In some embodiments, Form B is characterized in that it has a glass transition ($T_g$) of about 71° C. after quench cooling. In some embodiments, Form B is characterized in that it has a ΔCp of about 0.48 J/g after quench cooling.

Figure 4:
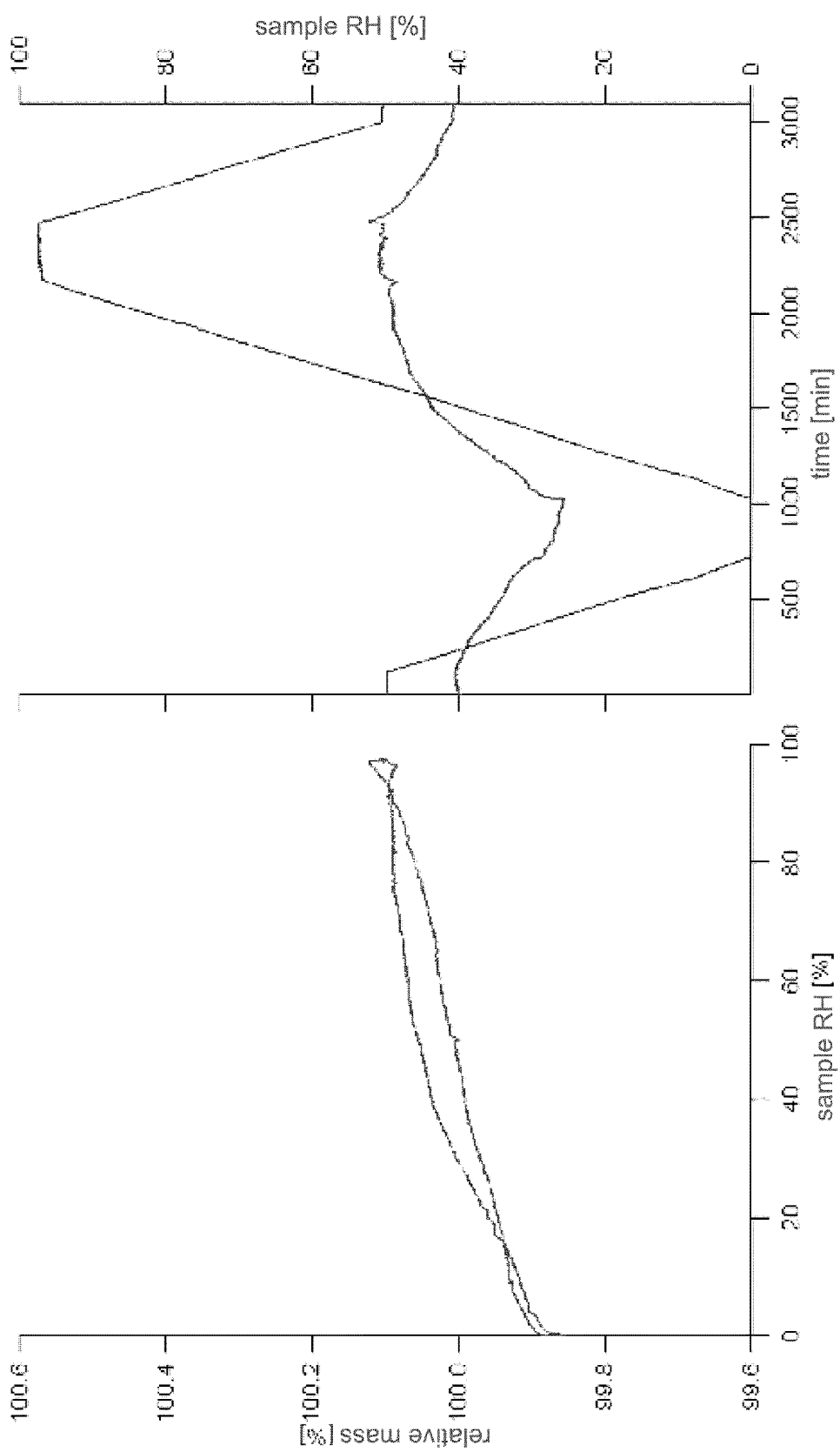
FIG. 4 depicts a Dynamic Vapor Sorption (DVS) isotherm of Form B.

In some embodiments, Form B has a DVS isotherm substantially similar to the one depicted in FIG. 4. In some embodiments, Form B is characterized in that it has a Δm of 0.1 wt % from 50% relative humidity (r.h.) to 85% r.h.

Figure 5:
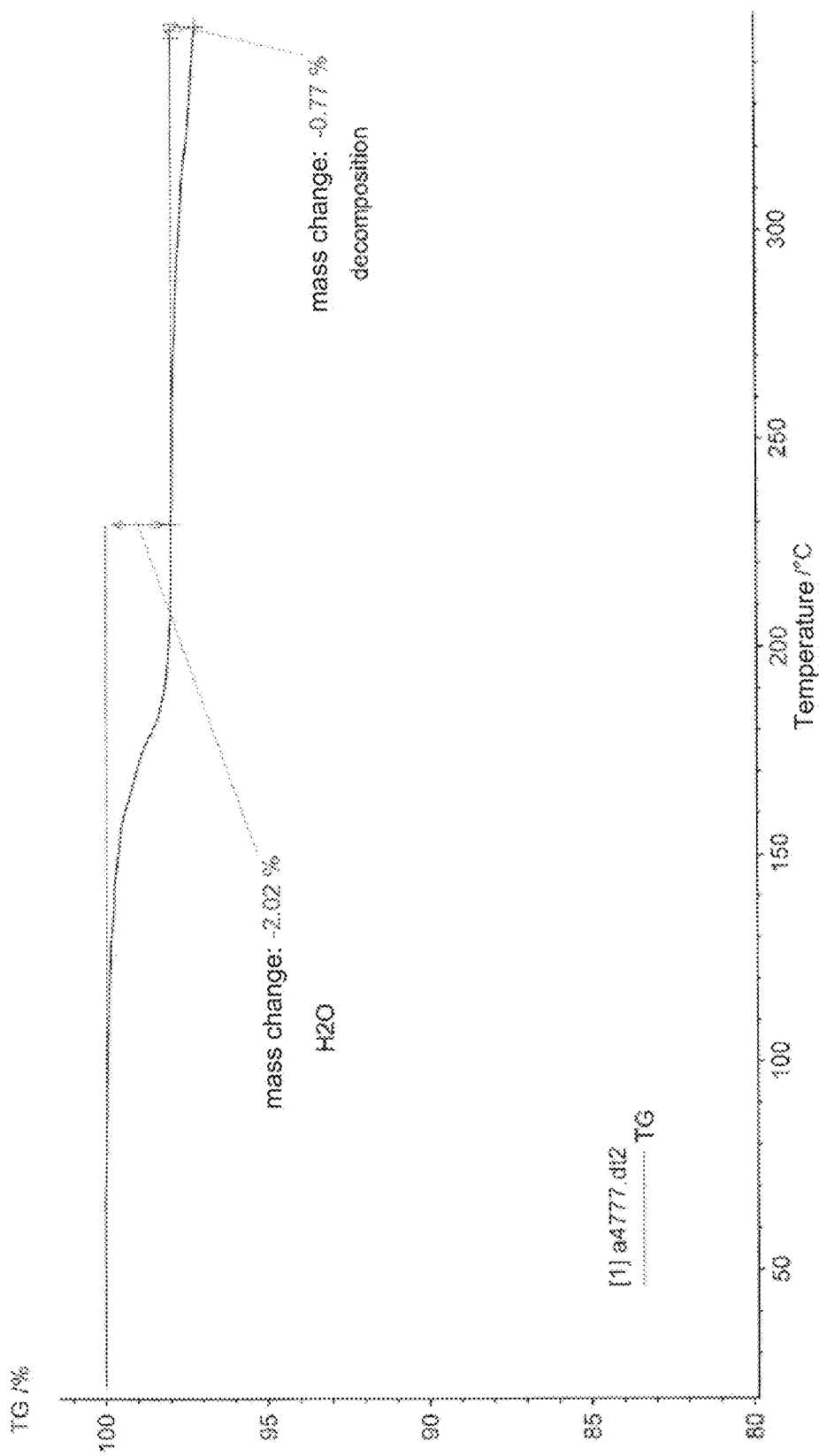
FIG. 5 depicts a Thermogravimetric Fourier-Transform Infrared (TG-FTIR) thermogram of Form B.

In some embodiments, Form B has a TG-FTIR thermogram substantially similar to the one depicted in FIG. 5. In some embodiments, Form B is characterized in that it losses about 2.0 wt % or 0.5 equivalent (eq.) of $H_2O$ after the temperature of Form B is increased from about 100° C. to about 230° C.

In some embodiments, Form B has a microscopic image substantially similar to the one depicted in FIG. 7A or FIG. 7B. In some embodiments, Form B is granular crystals.

In some embodiments, Form B has an observed melting point of about 155-168° C.

In some embodiments, Form B is stable for at least about 1 month, at least about 2 months, at least about 4 months, at least about 6 months, at least about 12 months, at least about 18 months, at least about 24 months, or at least about 3 years at about 25° C. and about 60% relative humidity. In some embodiments, Form B has substantially the same XRPD pattern post storage for at least about 1 month, at least about 2 months, at least about 4 months, at least about 6 months, at least about 12 months, at least about 18 months, at least about 24 months, or at least about 3 years at about 25° C. and about 60% relative humidity. In some embodiments, Form B has substantially the same IR spectrum post storage for at least about 1 month, at least about 2 months, at least about 4 months, at least about 6 months, at least about 12 months, at least about 18 months, at least about 24 months, or at least about 3 years at about 25° C. and about 60% relative humidity.

In some embodiments, Form B is stable for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity. In some embodiments, Form B has substantially the same XRPD pattern post storage for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity. In some embodiments, Form B has substantially the same IR spectrum post storage for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity.

Pharmaceutical Compositions

In some embodiments, the present invention provides a composition comprising crystalline Form B of compound 1 described herein and optionally a pharmaceutically acceptable excipient. In certain embodiments, the pharmaceutical compositions are useful for treating a disease, disorder, or condition described herein. In certain embodiments, a provided composition is formulated for administration to a subject in need of such composition. In certain embodiments, a provided composition is formulated for oral administration to a subject. In certain embodiments, a provided composition is formulated into an oral dosage form. In certain embodiments, a provided composition is formulated into a tablet, powder, pill, capsule, or the like, for oral ingestion by a subject.

Suitable techniques, carriers, and excipients include those found within, for example, *Remington: The Science and Practice of Pharmacy*, 19$^{th}$ edition, Mack Publishing Company, Easton, Pa. 1995; Hoover, John E., *Remington's Pharmaceutical Sciences*, Mack Publishing Company, Easton, Pa. 1975; Liberman, H. A. and Lachman, L., Eds., *Pharmaceutical Dosage Forms*, Marcel Decker, New York, N.Y. 1980; and *Pharmaceutical Dosage Forms, and Drug Delivery Systems*, 7$^{th}$ edition, Lippincott Williams & Wilkins, 1999, all of which are incorporated herein by reference in their entireties.

In general, doses of provided pharmaceutical compositions employed for adult human treatment are typically in the range of about 0.01 mg to about 5000 mg per day. In certain embodiments, doses employed for adult human treatment are from about 1 mg to about 1000 mg per day. In certain embodiments, a desired dose is conveniently presented in a single dose or in divided doses administered simultaneously (or over a short period of time) or at appropriate intervals, for example, as two, three, four or more sub-doses per day.

It will be understood that a specific dosage and treatment regimen for any particular subject may depend on a variety of factors, including the activity of the specific compound employed, age, body weight, general health, sex, diet, time of administration, rate of excretion, drug combination, and the judgment of the treating physician and the severity of the particular disease being treated. The amount of a provided compound in the composition may also depend upon the particular compound in the composition.

Methods of Preparing Form B

The present invention also provides methods of preparing Form B. In certain embodiments, methods of preparing Form B comprise mixing a solution of compound 1 in methanol with an aqueous solution of a base to provide a mixture. In certain embodiments, the methods of preparing Form B further comprise lowering the temperature of the mixture to provide a solid. In certain embodiments, the methods of preparing Form B further comprise isolating the solid from the mixture.

Compound 1 useful in the preparation of Form B may be substantially free of impurities. In certain embodiments, compound 1 useful in the preparation of Form B is about 90% free of impurities. In certain embodiments, compound 1 useful in the preparation of Form B is about 92% free of impurities. In certain embodiments, compound 1 useful in the preparation of Form B is about 95% free of impurities. In certain embodiments, compound 1 useful in the preparation of Form B is about 97% free of impurities. In certain embodiments, compound 1 useful in the preparation of Form B is about 99% free of impurities. In certain embodiments, compound 1 useful in the preparation of Form B is about 99.5% free of impurities. In certain embodiments, compound 1 useful in the preparation of Form B includes compound 2 as an impurity:

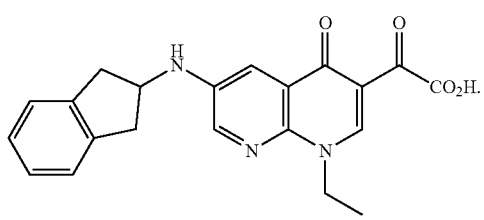

2

Compound 1 may be present in the solution of compound 1 and methanol at any suitable concentration (e.g., about 0.003 kg/L, about 0.01 kg/L, about 0.02 kg/L, about 0.03 kg/L, about 0.04 kg/L, about 0.05 kg/L, about 0.06 kg/L, about 0.08 kg/L, about 0.1 kg/L, about 0.2 kg/L, about 0.5 kg/L, or about 1 kg/L), as the solubility of compound 1 permits. In certain embodiments, the concentration of compound 1 in the solution of compound 1 and methanol is about 0.04 kg/L.

The base useful in the preparation of Form B may be any inorganic base. In certain embodiments, the inorganic base is ammonia. In certain embodiments, the inorganic base is ammonium carbonate. In certain embodiments, the inorganic base is ammonium hydroxide. In certain embodiments, the inorganic base is an alkali metal carbonate. In certain embodiments, the inorganic base is $Li_2CO_3$, $Na_2CO_3$, $K_2CO_3$, $Rb_2CO_3$, or $Cs_2CO_3$. In certain embodiments, the inorganic base is an alkali metal bicarbonate. In certain embodiments, the inorganic base is $LiHCO_3$, $NaHCO_3$, $KHCO_3$, $RbHCO_3$, or $CsHCO_3$. In certain embodiments, the inorganic base is an alkali metal hydroxide. In certain embodiments, the inorganic base is LiOH, NaOH, KOH, RbOH, or CsOH. In certain embodiments, the inorganic base is an alkaline earth metal carbonate. In certain embodiments, the inorganic base is $BeCO_3$, $MgCO_3$, $CaCO_3$, $SrCO_3$, or $BaCO_3$. In certain embodiments, the inorganic base is an alkaline earth metal bicarbonate. In certain embodiments, the inorganic base is $Be(HCO_3)_2$, $Mg(HCO_3)_2$, $Ca(HCO_3)_2$, $Sr(HCO_3)_2$, or $Ba(HCO_3)_2$. In certain embodiments, the inorganic base is an alkaline earth metal hydroxide. In certain embodiments, the inorganic base is $Be(OH)_2$, $Mg(OH)_2$, $Ca(OH)_2$, $Sr(OH)_2$, or $Ba(OH)_2$. The base useful in the preparation of Form B may also be an organic base. In certain embodiments, the organic base is an aliphatic amine. In certain embodiments, the organic base is an aromatic amine. In certain embodiments, the organic base is a primary amine. In certain embodiments, the organic base is a secondary amine. In certain embodiments, the organic base is a tertiary amine. In certain embodiments, the organic base is triethylamine, DIPEA, or DBU. In certain embodiments, the organic base is substituted pyridine. In certain embodiments, the organic base is 2,6-lutidine or DMAP. In certain embodiments, the organic base is unsubstituted pyridine. The base may be present in the aqueous solution at any suitable concentration (e.g., about 0.01 g/L, about 0.03 g/L, about 0.1 g/L, about 0.2 g/L, about 0.3 g/L, about 0.4 g/L, about 0.5 g/L, about 0.7 g/L, about 1 g/L, about 3 g/L, about 10 g/L, or about 30 g/L), as the solubility of the base permits. In certain embodiments, the base is present in the aqueous solution at about 0.2 g/L.

In certain embodiments, the solution of compound 1 in methanol is substantially homogeneous. In certain embodiments, the solution of compound 1 in methanol is substantially free of solid materials. In certain embodiments, the aqueous solution of the base is substantially homogeneous. In certain embodiments, the aqueous solution of the base is substantially free of solid materials. In certain embodiments, the mixture of the inventive methods is a substantially homogeneous solution. In certain embodiments, the mixture is heterogeneous. In certain embodiments, the mixture comprises a solid. In certain embodiments, the mixture comprises a solid and a liquid. In certain embodiments, the mixture comprises Form B. In certain embodiments, the mixture comprises Form B that is substantially free of impurities.

When the mixture of the inventive methods comprises a solid, the solid may be isolated from the mixture by a process known in the art, such as by filtration and/or centrifuge. The solid isolated form the mixture may optionally be subject to a reduced pressure and/or a suitable temperature as described herein. In certain embodiments, the solid in the mixture comprises Form B. In certain embodiments, the solid in the mixture comprises Form B that is substantially free of impurities. In certain embodiments, the solid isolated from the mixture comprises Form B. In certain embodiments, the solid isolated from the mixture comprises Form B that is substantially free of impurities. In certain embodiments, the solid isolated from the mixture comprises at least 99%, at least 99.2%, at least 99.4%, at least 99.5%, at least 99.6%, at least 99.7%, at least 99.8%, at least 99.9%, at least 99.95%, at least 99.99%, at least 99.995%, or at least 99.999% Form B by weight.

The steps of preparing Form B may be performed at any suitable temperature, e.g., a suitable temperature of at least about 60° C. and lower than about 65° C. Other ranges are also possible. In certain embodiments, the suitable temperature is about 0° C. In certain embodiments, the suitable temperature is about 23° C. In certain embodiments, the suitable temperature is about 60° C. In certain embodiments, the suitable temperature is about 65° C. A suitable temperature may be a variable temperature during one or more steps of a method of the invention. In certain embodiments, the temperature of the solution of compound 1 in methanol is a suitable temperature described herein (e.g., about 60 to 65° C.). In certain embodiments, the temperature of the aqueous solution of the base is a suitable temperature described herein (e.g., about 60 to 65° C.). The temperature of the solution of compound 1 in methanol and the temperature of the aqueous solution of the base may be the same or different. In the step of lowering the temperature of the mixture, the temperature of the mixture may be lowered by about 10° C., about 20° C., about 30° C., about 35° C., about 40° C., about 45° C., about 50° C., about 60° C., about 65° C., about 70° C., about 80° C., about 90° C., or about 100° C. In certain embodiments, the temperature of the mixture is lowered by at least about 35 and less than about 45° C. In certain embodiments, the mixture is substantially homogeneous before the temperature of it is lowered. In certain embodiments, the mixture is substantially free of solid materials before the temperature of the mixture is lowered. In certain embodiments, the mixture is heterogeneous after the temperature of it is lowered. In certain embodiments, the mixture comprises a solid after the temperature of the mixture is lowered. In certain embodiments, the mixture comprises a solid and a liquid after the temperature of the mixture is lowered.

A suitable condition may also include a suitable pressure under which one or more steps of the inventive methods are performed. In certain embodiments, the suitable pressure is about 1 atmosphere. A suitable pressure may also be higher or lower than 1 atmosphere (i.e., a reduced pressure). A reduced pressure may be a pressure lower than about $10^{-1}$ atmosphere, lower than about $10^{-2}$ atmosphere, lower than about $10^{-3}$ atmosphere, lower than about $10^{-4}$ atmosphere, lower than about $10^{-5}$ atmosphere, lower than about $10^{-6}$ atmosphere, lower than about $10^{-7}$ atmosphere, lower than about $10^{-8}$ atmosphere, lower than about $10^{-9}$ atmosphere, lower than about $10^{-10}$ atmosphere, or lower than about $10^{-11}$ atmosphere.

A suitable condition may also include a suitable atmosphere under which one or more steps of the inventive methods are performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that one or more steps of the method lasts. In certain embodiments, the suitable time duration is in the order of minutes (e.g., about 30 min), hours (e.g., about 1 hour, about 2 hours, about 3 hours, about 6 hours, or about 12 hours), days (e.g., about 1 day or about 2 days) or weeks (e.g., about 1 week). For example, in the step of lowering the temperature of the mixture, the temperature of the mixture may be lowered over a suitable time duration described herein.

Treatment Methods

The present disclosure contemplates the treatment or prophylaxis of a disease of the central nervous system, such as mood disorders (e.g., depression), anxiety disorders, and neurodegenerative diseases. The term neurodegenerative disease encompasses a condition leading to the progressive loss of structure or function of neurons, including death of neurons. Examples of neurodegenerative diseases contemplated herein include AIDS dementia complex, adrenoleukodystrophy, alexander disease, Alpers' disease, amyotrophic lateral sclerosis, ataxia telangiectasia, Batten disease, bovine spongiform encephalopathy, brainstem and cerebellum atrophy, Canavan disease, corticobasal degeneration, Creutzfeldt-Jakob disease, dementia with Lewy bodies, fatal familial insomnia, Friedrich's ataxia, familial spastic paraparesis, frontotemporal lobar degeneration, Huntington's disease, infantile Refsum disease, Kennedy's disease, Krabbe disease, Lyme disease, Machado-Joseph disease, monomelic amyotrophy, multiple sclerosis, multiple system atrophy, neuroacanthocytosis, Niemann-Pick disease, neurodegeneration with brain iron accumulation, opsoclonus myoclonus, Parkinson's disease, Pick's disease, primary lateral sclerosis, progranulin, progressive multifocal leukoencephalopathy, progressive supranuclear palsy, protein aggregation, Refsum disease, Sandhoff disease, diffuse myelinoclastic sclerosis, Shy-Drager syndrome, spinocerebellar ataxia, spinal muscular atrophy, spinal and bulbar muscular atrophy, subacute combined degeneration of spinal cord, Tabes *dorsalis*, Tay-Sachs disease, toxic encephalopathy, transmissible spongiform encephalopathy, and Wobbly hedgehog syndrome.

In certain embodiments, compound 1, and/or one or more pharmaceutical compositions of compound 1, can be used to treat, ameliorate the signs and/or symptoms of, prevent, or otherwise delay the onset or development of the CNS disease, disorder, or condition.

Taught herein, therefore, is the use of compound 1, and/or one or more pharmaceutical compositions of compound 1 described herein, or a pharmaceutically acceptable preparation thereof, in the manufacture of a medicament for treating and/or preventing central nervous system disorders, such as mood disorders (e.g., depression), anxiety disorders, or neurodegenerative diseases, in a subject in need thereof.

Also provided herein are methods of treating and/or preventing central nervous system disorders, such as mood disorders (e.g., depression), anxiety disorders, or neurodegenerative diseases comprising the administration of an effective amount of compound 1, and/or one or more pharmaceutical compositions of compound 1 described herein, or a pharmaceutically acceptable preparation thereof, to a subject in need thereof.

As used herein mood disorders are broadly recognized and clearly defined by the relevant DSM-IV-TR (Diagnostic and Statistical Manual of Mental Disorders, 4th Edition, Text Revision) criteria. Thus, there are depressive disorders of which the best known and most researched is major depressive disorder (MDD) commonly called clinical depression or major depression, and bipolar disorder (BD), formerly known as manic depression and characterized by intermittent episodes of mania or hypomania, usually interlaced with depressive episodes. Other depressive disorders include: atypical depression, melancholic depression, psychotic major depression, catatonic depression, postpartum depression, seasonal affective disorder, dysthymia, depressive disorder not otherwise specified (DD-NOS) (e.g., recurrent brief depression, minor depressive disorder), substance induced mood disorders (e.g., alcohol induced mood disorders, benzodiazepine induced mood disorders, interferon-alpha induced mood disorders).

Persons of skill in the art will be familiar with the lag period of traditional antidepressant medications, and with the heightened anxiety produced by the newer generation antidepressants, including SSRI's, SNRI's and NRI's in the early stages of treatment before the antidepressant effects are seen (within 2-4 weeks). Thus, in certain embodiments, the compounds described herein can be administered to a subject in need thereof as a substitute or replacement for traditional antidepressant medication. In other embodiments, compounds described herein can be administered to a subject in need thereof as a supplement to traditional antidepressant medication. In other embodiments, there is provided a method for treating or preventing depression in a subject, the method including the step of administering to said subject a compound (e.g., Form B of compound 1), or an embodiment thereof, described herein, or a pharmaceutical composition thereof, in the absence of adjunct antidepressant therapy.

Replacing traditional antidepressant medication with the present compounds can be advantageous, particularly where the traditional medication is associated with one or more adverse effects (e.g., anxiety, nausea, headaches, erectile dysfunction, early-onset suicidal tendencies, etc). Examples of traditional antidepressant medication would be known to those skilled in the art and include, but are not limited to, selective serotonin re-uptake inhibitors (SSRI), serotonin/noradrenalin re-uptake inhibitors, selective noradrenalin re-uptake inhibitors, monoamine oxidase inhibitors, tricyclic antidepressants, lithium and other mood stabilisers, atypical antidepressants, and hormones such as estrogen or progestogen.

In other embodiments, the present compounds are administered to a subject in need thereof, together with traditional antidepressants for a period of about 2-4 weeks, to address the symptoms of depression, with the option of discontinuing treatment with the present compounds whilst continuing with the traditional therapy. In other embodiments, the subject is treated with both a present compound and one or more traditional antidepressant medications (administered sequentially or in combination) for the duration of the treatment period. Such combination therapy may be particularly useful, for example, where the combination of a present compound and one or more traditional antidepressant medications provides relief from depression in the acute lag phase of the treatment period and/or where an additive or synergistic antidepressant therapeutic effect is desired.

Depression relapse can also occur in patients treated with traditional antidepressant medication. Many such compounds are administered for anywhere from months to years and a reduction in efficacy is often seen with such long-term use, leading to significant continuing depression and, dysfunction. Depression relapse may be sudden onset for some patients, while for others it might be evident as a gradual decline in mood and function, which diminishes over time as the patient approaches the state of relapse. Thus, patients who experience sudden onset of depression relapse or a gradual depression relapse would benefit from the methods disclosed herein, as the present compound, or pharmaceutical compositions thereof, can offset the diminishing effect of traditional antidepressant therapy. Thus, the use of the present compound, or pharmaceutical compositions thereof may prevent or partly alleviate depression relapse often seen in patients taking traditional antidepressant medication.

Thus, in certain embodiments, provided herein are methods for treating or preventing relapse in a subject receiving antidepressant therapy, the method including the step of administering to said subject Form B of compound 1, or a pharmaceutical composition thereof.

The traditional antidepressant therapies that are associated with potential depression relapse in a subject would be known to those skilled in the art. Examples include, but are not limited to, dosage increases, alternative SSRIs or SNRIs, and non-SSRI antidepressants such as noradrenaline re-uptake inhibitors, monoamine oxidase inhibitors, tricyclic antidepressants, lithium and other mood stabilisers, atypical antidepressants and hormones such as estrogen and progestogen, also referred to herein as "second antidepressant compounds."

The desired therapeutic activity, or effect, will typically depend on the condition being treated. For example, where the subject is being treated for depression, the therapeutic effect may be a reduction in at least one clinical symptom of depression, including, but not limited to, cognitive impairment, loss of appetite, mood, and/or inactivity.

In certain embodiments, compound 1, or pharmaceutical compositions thereof described herein, or a pharmaceutically acceptable preparation thereof, is administered to said subject sequentially (i.e., before or after) or in combination with a second antidepressant compound (e.g., with existing antidepressant therapy).

In certain embodiments, the present compound, or pharmaceutical compositions thereof, have the further added advantage over traditional therapy in that they exhibit reduced sedative side effects which may adversely affect a subject's quality of life. In certain embodiments, the present compound, or pharmaceutical compositions thereof, are free of measurable sedative side effects.

Sudden discontinuation of antidepressant medication may produce withdrawal effects caused by physical dependence on the drug. Compounds can be evaluated for physical dependence in a simple animal model where, following a period of chronic dosing (e.g., for 14-20 days), the study drug is stopped and measurements of food intake, body weight and body temperature are taken over the next 5 days. The symptoms of abrupt discontinuation of the drug are manifest as significantly reduced appetite, weight loss, and drop in body temperature. This model is suitable for detecting the effects across a broad range of drug classes including opiates, antidepressants, and benzodiazepines. The compound, or pharmaceutical compositions thereof described herein also can be used as a combination therapy, e.g., combining the treatment with other antidepressants such as benzodiazepines (e.g., alprazolam, diazepam, lorazepam, clonezepam), selective serotonin re-uptake inhibitors (SSRI) (e.g., citalopram, dapoxetine, escitalopram, fluoxetine, fluvoxamine, indalpine, paroxetine, sertraline, zimelidine, vilaxodone), serotonin norepinephrine reuptake inhibitors (SNRI) (e.g., venlafaxine, duloxetine, desvenlafaxine, milnacipran), monoamine oxidase inhibitors (e.g., phenelzine, moclobemide), tricyclic antidepressants (e.g., trimipramine, imipramine), tetracyclic antidepressants (e.g., mertazepine, maprotiline), mood stabilisers (e.g. lithium, sodium valproate, valproic acid), atypical antidepressants (e.g., bupropion), acetylcholinesterase inhibitors (e.g., donepezil, galantamine, rivastigmine), atypical antipsychotics (e.g., risperidone, aripiprizole, quetiapine, olanzapine), and hormones such as estrogen and progestogen.

It will thus be understood that compound 1, or pharmaceutical compositions thereof, can be used in the treatment and/or prevention of any disease state, disorder, or condition which may be ameliorated by enhancement of neurite outgrowth.

In certain embodiments, the neurite outgrowth-responsive disease is a neurodegenerative disease. In a certain embodiments, the neurodegenerative disease is multiple sclerosis or a Parkinsonian related disorder. In a further embodiment, the neurodegenerative disease is multiple sclerosis. In a further embodiment the disease may involve a condition which involves neural damage including wound healing, spinal cord injury, peripheral nerve disorders.

Also contemplated herein is a sub-threshold disease, condition, state, disorder or trauma. In an embodiment, the disease, condition, state, disorder, or trauma is defined by its symptoms. Hence, compound 1, or a pharmaceutical composition thereof contemplated herein, is useful in ameliorating the symptoms of a disease, condition, state, disorder, or trauma of the CNS. By "trauma" this includes stroke, brain haemorrhage, or another condition or event of the systemic vasculature which affects the CNS. The symptoms of a disease, condition, state, disorder, or trauma of the CNS would be familiar to those skilled in the art. Examples of such symptoms include mood disorders, such as depression. Thus, in certain embodiments, the compound forms described herein are used in the treatment of depression attributed to (or associated with) a neurodegenerative disease in the subject.

The compound forms described herein may also be used as therapy, e.g., combining the treatment with other neurodegenerative treatments, such as acetylcholinesterase inhibitors (e.g., Aricept, Exelon), and treatments for multiple sclerosis (e.g., Avonex, Betaseron, Copaxone, Tysabri, Gilenya).

In a further embodiment there is also provided a method of treatment of disorders of the central nervous system comprising the administration of an effective amount of compound 1, or a pharmaceutical composition thereof, to a subject in need thereof.

It will be understood that compound 1, or a pharmaceutical composition thereof as described herein, can be used in the treatment of anxiety or conditions/disease states associated with anxiety such as irritable bowel syndrome and fibromyalgia.

In certain embodiments, an anxiety disorder is classified as one of the following:
panic disorder,
obsessive-compulsive disorder (OCD),
post-traumatic stress disorder (PTSD),
social phobia (or social anxiety disorder—SAD),
specific phobias,
generalized anxiety disorder (GAD),
substance-induced anxiety disorder, and
acute stress disorder (ASD).

In certain embodiments, compound 1, or a pharmaceutical composition thereof, as described herein may be used in the treatment of a panic disorder.

In certain embodiments, compound 1, or a pharmaceutical composition thereof, as described herein may be used in the treatment of obsessive-compulsive disorder (OCD).

In certain embodiments, compound 1, or a pharmaceutical composition thereof, as described herein may be used in the treatment of post-traumatic stress disorder (PTSD).

In an embodiment compound 1, or a pharmaceutical composition thereof, as described herein may be used in the treatment of social phobia (or social anxiety disorder—SAD).

In certain embodiments, compound 1, or a pharmaceutical composition thereof, as described herein may be used in the treatment of specific phobias. In certain embodiments, compound 1 or a pharmaceutical composition thereof, as described herein may be used for agoraphobia or agoraphobia without history of panic disorder. In certain embodiments, compound 1 or a pharmaceutical composition thereof, as described herein may be used for animal phobia.

In certain embodiments, compound 1, or a pharmaceutical composition thereof, as described herein may be used in the treatment of substance-induced anxiety disorder.

In certain embodiments, compound 1, or a pharmaceutical composition thereof, as described herein may be used in the treatment of acute stress disorder (ASD).

In certain embodiments, compound 1, or a pharmaceutical composition thereof, as described herein may be used in the treatment of generalized anxiety disorder (GAD).

Generalised anxiety disorder criteria include:
(i) At least 6 months of "excessive anxiety and worry" about a variety of events and situations. Generally, "excessive" can be interpreted as more than would be expected for a particular situation or event. Most people become anxious over certain things, but the intensity of the anxiety typically corresponds to the situation.
(ii) There is significant difficulty in controlling the anxiety and worry. If someone has a very difficult struggle to regain control, relax, or cope with the anxiety and worry, then this requirement is met.
(iii) The presence for most days over the previous six months of 3 or more (only 1 for children) of the following symptoms:
1. Feeling wound-up, tense, or restless
2. Easily becoming fatigued or worn-out
3. Concentration problems
4. Irritability
5. Significant tension in muscles
6. Difficulty with sleep
(iv) The symptoms are not part of another mental disorder.
(v) The symptoms cause "clinically significant distress" or problems functioning in daily life. "Clinically significant" is the part that relies on the perspective of the treatment provider. Some people can have many of the aforementioned symptoms and cope with them well enough to maintain a high level of functioning.
(vi) The condition is not due to a substance or medical issue.

In certain embodiments, a subject to be treated with compound 1, or a pharmaceutical composition thereof, as described herein may be identified by one or more of the above criteria for generalized anxiety disorder.

In certain embodiments, compound 1, or a pharmaceutical composition thereof, as described herein may be used to treat or prevent one or more symptoms associated with an anxiety disorder.

Each anxiety disorder has different symptoms, but all the symptoms cluster around excessive, irrational fear and dread.

In another embodiment compound 1, or a pharmaceutical composition thereof, as described herein may be used in the treatment of depression, for instance, major depressive disorder.

Major depressive disorder criteria include:

(i) At least five of the following symptoms have been present during the same 2-week period and represent a change from previous functioning: at least one of the symptoms is either
1) depressed mood or
2) loss of interest or pleasure.

(ii) Depressed mood most of the day, nearly every day, as indicated either by subjective report (e.g., feels sad or empty) or observation made by others (e.g., appears tearful).

(iii) Markedly diminished interest or pleasure in all, or almost all, activities most of the day, nearly every day (as indicated either by subjective account or observation made by others).

(iv) Significant weight loss when not dieting or weight gain (e.g., a change of more than 5% of body weight in a month), or decrease or increase in appetite nearly every day.

(v) Insomnia or hypersomnia nearly every day.

(vi) Psychomotor agitation or retardation nearly every day (observable by others, not merely subjective feelings of restlessness or being slowed down).

(vii) Fatigue or loss of energy nearly every day.

(viii) Feelings of worthlessness or excessive or inappropriate guilt (Which may be delusional) nearly every day (not merely self-reproach or guilt about being sick).

(ix) Diminished ability to think or concentrate, or indecisiveness, nearly every day (either by subjective account or as observed by others).

(x) Recurrent thoughts of death (not just fear of dying), recurrent suicidal ideation without a specific plan, or a suicide attempt or specific plan for committing suicide (xi) The symptoms do not meet criteria for a mixed episode.

(xii) The symptoms cause clinically significant distress or impairment in social, occupational, or other important areas of functioning.

(xiii) The symptoms are not due to the direct physiological effects of a substance (e.g. a drug of abuse, a medication) or a general medical condition (e.g., hypothyroidism).

(xiv) The symptoms are not better accounted for by bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

The above criteria have been sourced from the American Psychiatric Association (2000) Diagnostic and Statistical Manual of Mental Disorders (4th Ed., Text Revision). Washington D.C.: American Psychiatric Association.

In certain embodiments, a subject to be treated with compound 1, or a pharmaceutical composition thereof, as described herein may be identified by one or more of the above criteria for major depressive disorder.

In another embodiment compound 1, or a pharmaceutical composition thereof, as described herein may be used to treat or prevent one or more symptoms associated with depression.

Further disorders for which compound 1, or a pharmaceutical composition thereof, as described herein may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic subjects; hearing disorders, including tinnitus and age-related hearing impairment; urinary incontinence; and the effects of substance abuse or dependency, including alcohol withdrawal, neuroses, convulsions, migraine, depressive disorder, bipolar disorder, psychotic disorder, neurodegeneration arising from cerebral ischemia, attention deficit hyperactivity disorder, Tourette's syndrome, speech disorder, disorders of circadian rhythm, single-episode or recurrent major depressive disorder, dysthymic disorder, bipolar I or bipolar II manic disorder, cyclothymic disorder, schizophrenia, and stuttering.

In an embodiment compound 1, or a pharmaceutical composition thereof, as described herein may be used in the treatment of cerebral ischemia. In certain embodiments, compound 1, or a pharmaceutical composition thereof, as described herein may be used in the treatment of neurodegeneration arising from cerebral ischemia.

In an embodiment compound 1, or a pharmaceutical composition thereof, as described herein may be used in the treatment of disorders of the circadian rhythm.

In an embodiment compound 1, or a pharmaceutical composition thereof, as described herein may be used in the treatment of pain and nociception.

In an embodiment compound 1, or a pharmaceutical composition thereof, as described herein may be used in the treatment of Alzheimer's disease.

It should be appreciated that compound 1, or a pharmaceutical composition thereof, a described herein can be administered to a subject in a treatment effective amount. In some embodiments, a treatment effective amount is a therapeutically effective amount or a prophylactically effective amount. The term "therapeutically effective amount" as used herein means that amount of active compound or pharmaceutical agent that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the subject is protected against worsening of this process).

As used herein, the term "effective amount" relates to an amount of a compound, or pharmaceutical composition thereof, which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 µg to, 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

In certain embodiments, a provided method comprises administering to a subject in need thereof the present compound, or pharmaceutical composition thereof, in a dosage to provide an effective amount in vivo that will enhance neurite outgrowth (neurogenesis), including, but not limited to the acute stages of treatment (e.g., within 1, 2, 3, or 4 weeks from the commencement of treatment). In an embodiment, an effective amount in vivo has an in vitro equivalent concentration that is sufficient to increase neurite outgrowth by at least 5%, at least 10%, at least 20%, or at least 50% in a neurite outgrowth assay, for example, a neurite outgrowth assay described herein. Methods of determining an in vitro equivalent concentration of the present compounds would be familiar to the skilled artisan. For example, at from about 10 minutes to about 60 minutes after administration of the present compounds to a subject, a blood sample is taken and assayed by HPLC, ELISA, gas chromatography, or by other suitable assay to determine the concentration per ml of blood. An equivalent effective concentration can then be used in an in vitro assay once factors such as the weight of the subject, the appropriate blood volume of the subject and the appropriate rate of diffusion of the present compound across the blood-brain barrier are taken into account. In another embodiment, when the present compound is found to stimulate neurite outgrowth in vitro (as compared to a control), an approximate in vivo effective amount can be determined for a subject by extrapolating the in vitro concentration to an in vivo equivalent. Factors such as the weight of the subject, the appropriate blood volume of the subject and the appropriate rate of diffusion of the present compound across the blood-brain barrier may be used to extrapolate an in vivo effective amount and hence the appropriate dosage amount that would give rise to said in vivo effective amount.

Thereafter, treatment with the compound 1, or a pharmaceutical composition thereof, may be continued throughout the treatment period or it may be ceased or replaced with traditional therapeutic compounds. Methods of determining the effective amount of compound 1, or a pharmaceutical composition thereof, that is required for enhancing neurite outgrowth (neurogenesis) in vivo would be familiar to those skilled in the art. For example, enhancement of neurogenesis can be determined by measuring a symptom of the CNS disorder including, but not limited to, cognitive impairment, degree and frequency of seizures or tremors, motordysfunction, headaches and mood (e.g., degree of happiness).

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of compound 1, or a pharmaceutical composition thereof, for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, compound 1, or a pharmaceutical composition thereof, may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another anti-anxiety or anti-depressant medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of compound 1, or a pharmaceutical composition thereof, and a second amount of an additional suitable therapeutic agent.

In certain embodiments, compound 1 or a pharmaceutical composition thereof as described herein, and the additional therapeutic agent are each administered in an effective amount (i.e., each in an amount which would be therapeutically effective if administered alone). In other embodiments, compound 1 or a pharmaceutical composition thereof as described herein, and the additional therapeutic agent are each administered in an amount which alone does not provide a therapeutic effect (a sub-therapeutic dose). In yet other embodiments, compound 1 or a pharmaceutical composition thereof as described herein can be administered in an effective amount, while the additional therapeutic agent is administered in a sub-therapeutic dose. In still other embodiments, compound 1 or a pharmaceutical composition thereof as described herein, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of compound 1 or a pharmaceutical composition thereof as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, compound 1 or a pharmaceutical composition thereof as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of therapeutic agents that may be combined with compound 1, or a pharmaceutical composition thereof, either administered separately or in the same pharmaceutical composition, include, but are not limited to, muscle relaxants, anticonvulsants, hypnotics, anesthetics, analgesics, cholinergics, antidepressants, mood stabilisers, and anxiolytics.

In certain embodiments, a second therapeutic agent is a SSRI selected from the following: citalopram (Celexa, Cipramil, Cipram, Dalsan, Recital, Emocal, Sepram, Seropram, Citox, Cital), dapoxetine (Priligy), escitalopram (Lexapro, Cipralex, Seroplex, Esertia), fluoxetine (Prozac, Fontex, Seromex, Seronil, Sarafem, Ladose, Motivest, Flutop, Fluctin (EUR), Fluox (NZ), Depress (UZB), Lovan (AUS), Prodep (IND)), fluvoxamine (Luvox, Fevarin, Faverin, Dumyrox, Favoxil, Movox), paroxetine (Paxil, Seroxat, Sereupin, Aropax, Deroxat, Divarius, Rexetin, Xetanor, Paroxat, Loxamine, Deparoc), sertraline (Zoloft, Lustral, Serlain, Asentra), and vilazodone (Viibryd).

In certain embodiments, a second therapeutic agent is a tetracyclic antidepressant (TeCA) selected from the group consisting of: amoxapine (Amokisan, Asendin, Asendis, Defanyl, Demolox, Moxadil), maprotiline (Deprilept, Ludiomil, Psymion), mazindol (Mazanor, Sanorex), mianserin (Bolvidon, Depnon, Norval, Tolvon), mirtazapine (Remeron, Avanza, Zispin, Miro), and setiptiline (Tecipul).

In certain embodiments, a second therapeutic agent is a serotonin-noradrenaline reuptake inhibitor (SNRI) selected from the group consisting of: desvenlafaxine (Pristiq), duloxetine (Cymbalta, Ariclaim, Xeristar, Yentreve, Duzela), milnacipran (Ixel, Savella, Dalcipran, Toledomin), and venlafaxine (Effexor, Efexor).

In certain embodiments, a second therapeutic agent is a Noradrenaline reuptake inhibitor (NRI) selected from the group consisting of: atomoxetine (Tomoxetine, Strattera, Attentin), mazindol (Mazanor, Sanorex), reboxetine (Edronax, Norebox, Prolift, Solvex, Davedax, Vestra), and viloxazine (Vivalan, Emovit, Vivarint, Vicilan).

In certain embodiments, a second therapeutic agent is a monoamine oxidase inhibitor (MAOI) selected from the group consisting of: benmoxin (Nerusil, Neuralex), hydralazine (Apresoline), iproclozide (Sursum), iproniazid (Marsilid, Iprozid, Ipronid, Rivivol, Propilniazida), isocarboxazid (Marplan), isoniazid (Laniazid, Nydrazid), mebanazine (Actomol), nialamide (Niamid), octamoxin (Ximaol, Nimaol), phenelzine (Nardil, Nardelzine), pheniprazine (Catron), phenoxypropazine (Drazine), pivalylbenzhydrazine (Tersavid), procarbazine (Matulane, Natulan, Indicarb), caroxazone (Surodil, Timostenil), echinopsidine (Adepren), furazolidone (Furoxone, Dependal-M), linezolid (Zyvox, Zyvoxam, Zyvoxid), tranylcypromine (Parnate, Jatrosom), brofaromine (Consonar), metralindole (Inkazan), minaprine (Cantor), moclobemide (Aurorix, Manerix), pirlindole (Pirazidol), toloxatone (Humoryl), lazabemide (Pakio, Tempium), pargyline (Eutonyl), rasagiline (Azilect), and selegiline (Deprenyl, Eldepryl, Emsam).

In certain embodiments, a second therapeutic agent is a tricyclic antidepressant (TCA) selected from the group consisting of: amitriptyline (Tryptomer, Elavil, Tryptizol, Laroxyl, Sarotex, Lentizol), butriptyline (Evadene, Evadyne, Evasidol, Centrolese), clomipramine (Anafranil), desipramine (Norpramin, Pertofrane), dosulepin (Prothiaden, Dothep, Thaden and Dopress), doxepin (Aponal, Adapine, Doxal, Deptran, Sinquan, Sinequan, Zonalon, Xepin, Silenor), imipramine (Antideprin, Deprimin, Deprinol, Depsol, Depsonil, Dynaprin, Eupramin, Imipramil, Irmin, Janimine, Melipramin, Surplix, Tofranil), lofepramine (Gamanil, Tymelyt, Lomont), nortriptyline (Sensoval, Aventyl, Pamelor, Norpress, Allegron, Noritren, Nortrilen), Protriptyline (Vivactil), and trimipramine (Surmontil, Rhotrimine, Stangyl).

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

EXAMPLES

In order that the invention described herein may be more fully understood, the following examples are set forth. These examples are for illustrative purposes only and are not to be construed as limiting this invention in any manner.

Example 1

General Methods of Instrumental Measurements

FT-Raman Spectroscopy.
Bruker RFS100 with OPUS 6.5 software or Multi-RAM with OPUS 7.0 software; Nd:YAG 1064-nm excitation, Ge detector, 3500-100 cm$^{-1}$ range; typical measurement conditions: 50-300 mW nominal laser power, 64-128 scans, 2 cm$^{-1}$ resolution.

XRPD.
Bruker D8; reflection geometry, Bragg-Brentano; Cu—K$_\alpha$ radiation, 40 kV/40 mA; variable divergence slit; LynxEye detector with 3° window; 0.02° 2θ step size; 37 s step time. The samples were rotated during the measurement. Sample preparation: The samples were generally prepared without any special treatment other than the application of slight pressure to get a flat surface. Silicon single crystal sample holder, 0.1 mm deep.

$^1$H-NMR.
Bruker DPX300 spectrometer; proton frequency of 300.13 MHz; 30° excitation pulse; recycle delay of 1 s; accumulation of 16 scans; deuterated DMSO as the solvent; solvent peak used for referencing; chemical shifts reported on the TMS scale.

TG-FTIR.
Netzsch Thermo-Microbalance TG 209 with Bruker FT-IR Spectrometer Vector 22; aluminum crucible (with microhole), N$_2$ atmosphere, 10 K/min heating rate, 25-250° C. or 25-350° C. range.

DSC.
Perkin Elmer DSC 7; closed gold crucibles, sample filled in an N$_2$ environment, 10 K/min heating rate, −50 to 250° C. range, at times quench cooling (at −200 K min$^{-1}$) to −50° C. between scans.

DVS.
Projekt Messtechnik Sorptions Prüfsystem SPS 11-100n or Surface Measurement Systems DVS-1. The sample was placed on an aluminum or platinum holder on top of a microbalance and allowed to equilibrate for 2 h at 50% r.h. before starting one of two pre-defined humidity programs:
(1) 2 h at 50% r.h.;
(2) 50→0% r.h. (5%/h); 5 h at 0% r.h.;
(3) 0→95% r.h. (5%/h); 5 h at 95% r.h.; and
(4) 95→50% r.h. (5%/h); 2 h at 50% r.h.;
or
(1) 2 h at 50% r.h.;
(2) 50→95% r.h. (5%/h); 5 h at 95% r.h.;
(3) 95→0% r.h. (5%/h); 5 h at 0% r.h.; and
(4) 0→50% r.h. (5%/h); 2 h at 50% r.h.

The hygroscopicity was classified based on the mass gain at 85% r.h. relative to the initial mass as follows: deliquescent (sufficient water adsorbed to form a liquid), very hygroscopic (mass increase of ≥15%), hygroscopic (mass increase <15% and ≥2%), slightly hygroscopic (mass increase <2% and ≥0.2%), or non-hygroscopic (mass increase <0.2%).

Solvents.
For all experiments, Fluka, Merck or ABCR analytical grade solvents were used.

HPLC.
HPLC methods given in Table 6 were used. Standard solutions of the SP196-FD-P1 free drug of compound 1 and the L-malate salt of compound 1 (SP196-MLA-P4) were prepared in the concentration range of 0.2-0.05 mg/mL for the construction of a calibration curve.

TABLE 6

HPLC methods.

| | | | |
|---|---|---|---|
| Instrument | Agilent 1100 series | | |
| Column | Waters Xterra C18, 100 × 4.6 mm, 5 μm (FK-CC01E) | | |
| Mobile Phase A | H$_2$O + 0.1% TFA | | |
| Mobile Phase B | MeCN | | |
| Reference conc. | 0.2-0.05 mg/mL | | |
| Retention time | 10.48 min | | |
| Gradient | 0 min | 95% A | 5% B |
| | 20 min | 5% A | 95% B |
| | 20.5 min | 95% A | 5% B |
| | 22 min | 95% A | 5% B |
| Flow | 1.00 mL/min | | |
| Injection Volume | 10 μL | | |
| Column temp. | 25° C. | | |
| Wavelength | 240 nm | | |

Example 2

Preparation and Characterization of Form B 3.2 kg of compound 1 containing <0.5% impurity A (compound 2)) was dissolved in 100 L of methanol with refluxing, and 140 L of water at 72-75° C. was added. Upon completion of addition of water, the resulting mixture was allowed to cool very slowly to crystallize out a solid. The solid was isolated by filtration to give Form B in about 90% yield.

This method was fine-tuned to work on a kilogram scale. However, the impurity A was retained in crystallized material. The crystallization procedure was modified to remove any acidic impurity by using water containing Na$_2$CO$_3$ or NaHCO$_3$. Impurity A (compound 2) level was dropped from about 0.8% to about 0.1% after crystallization from MeOH and water containing Na$_2$CO$_3$ or NaHCO$_3$. In one set of experiments, 2.36 kg of compound 1 (containing 0.85% impurity A) was dissolved in 59 L of methanol with refluxing (60-65° C.) and 59 L of water (containing 11.8 g of Na$_2$CO$_3$) at 60-65° C. was added. Upon completion of addition of water, the mixture was allowed to cool very slowly to crystallize out a solid. The solid was separated by filtration to give Form B in about 90% yield (containing 0.1% impurity A). FT-Raman spectrum (FIG. 2) shows narrow, intense peaks and no fluorescence.

The XRPD pattern (FIG. 1) confirms the crystallinity of Form B.

Figure 6:
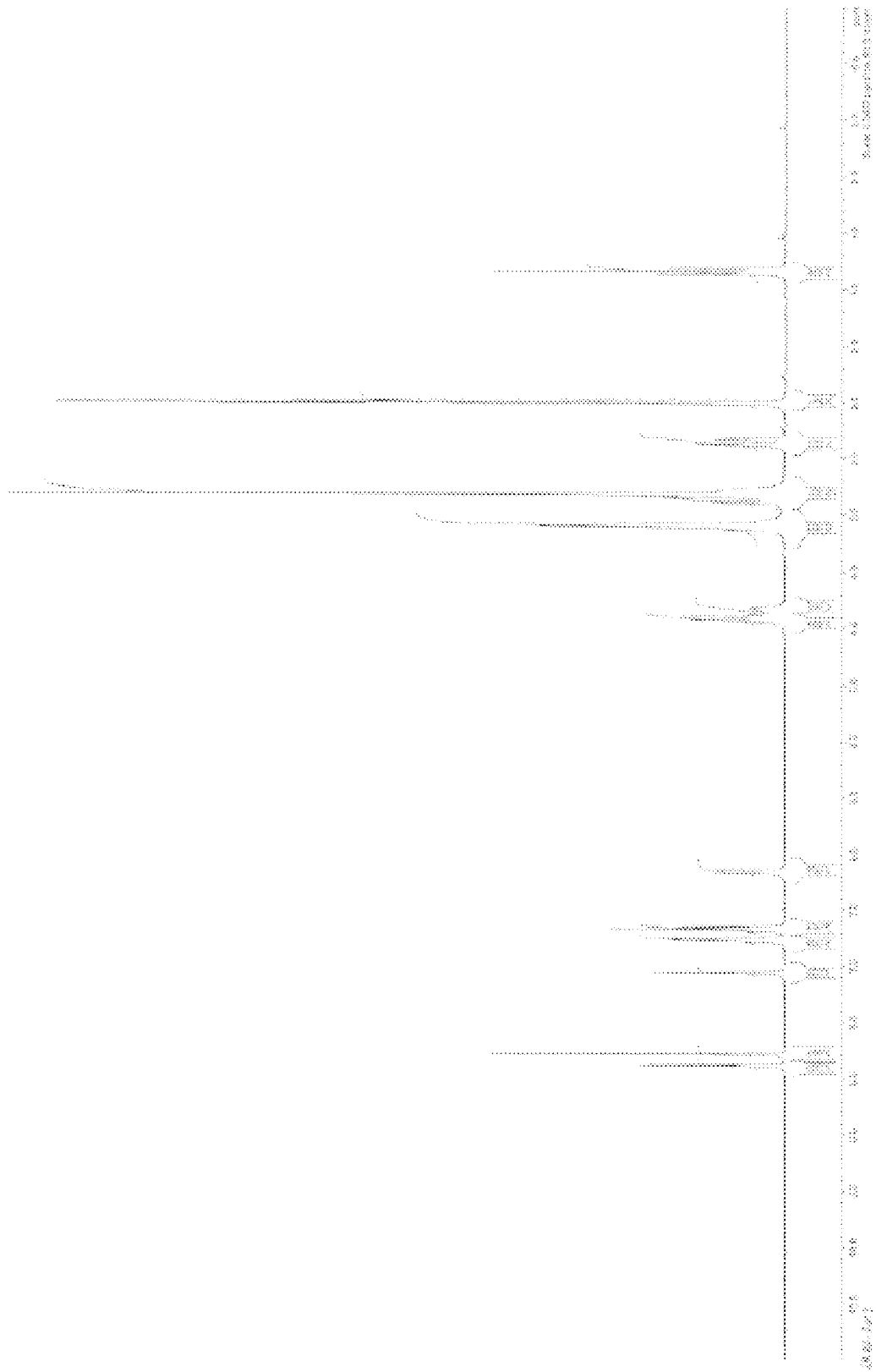
FIG. 6 depicts a Proton Nuclear Magnetic Resonance ($^1$H-NMR) spectrum of Form B.

The $^1$H-NMR spectrum (FIG. 6) agrees with the given structure.

The TG-FTIR thermogram (FIG. 5) shows the loss of about 2.0 wt % $H_2O$ between 100° C. and 230° C. and decomposition at >250° C. The water is most likely bound within the structure. The theoretical water content of a hemihydrate is 2.1 wt %. Thus, Form B is likely a hemihydrate and/or a non-stoichiometric hydrate.

The DSC thermogram (FIG. 3) shows an endotherm with several shoulders on the low temperature side and a peak maximum at a $T_{max}$ of about 176.3° C. (ΔH of about 105.4 J/g), most likely corresponding to melting. After quench cooling, a glass transition with a $T_g$ of about 70.8° C. (ΔCp of about 0.48 J/(g ° C.)) was observed in the second heating scan.

During the DVS measurement (FIG. 4), the relative humidity was first lowered from 50% r.h. to 0% r.h., then raised from 0% r.h. to 95% r.h. and lowered back again to 50% r.h. The sample shows a mass loss of about 0.1 wt % upon lowering the relative humidity from 50% r.h. to 0% r.h. Upon increasing the relative humidity to 95% r.h., a gradual mass gain of about 0.3 wt % (relative to the mass at 0% r.h.) was observed. Upon lowering the relative humidity from 95% r.h. to 50% r.h., the final mass was equal to the starting mass. The mass increase of 0.1 wt % at 85% r.h. (relative to the starting mass at 50% r.h.) classifies the sample as non-hygroscopic.

The FT-Raman spectrum of the sample of Form B after the DVS measurement is unchanged compared to the spectrum before the measurement, indicating that no transformation has taken place.

Microscopic images of the sample of Form B show that the sample consists of very small granular crystals (FIGS. 7A and 7B).

Example 3

Drying of Form B

A solid sample of Form B was dried in an attempt to dehydrate it. The sample was stored under vacuum (<5 mbar (e.g., about 4 mbar)) at 40° C. overnight or for 1 day.

Figure 8:
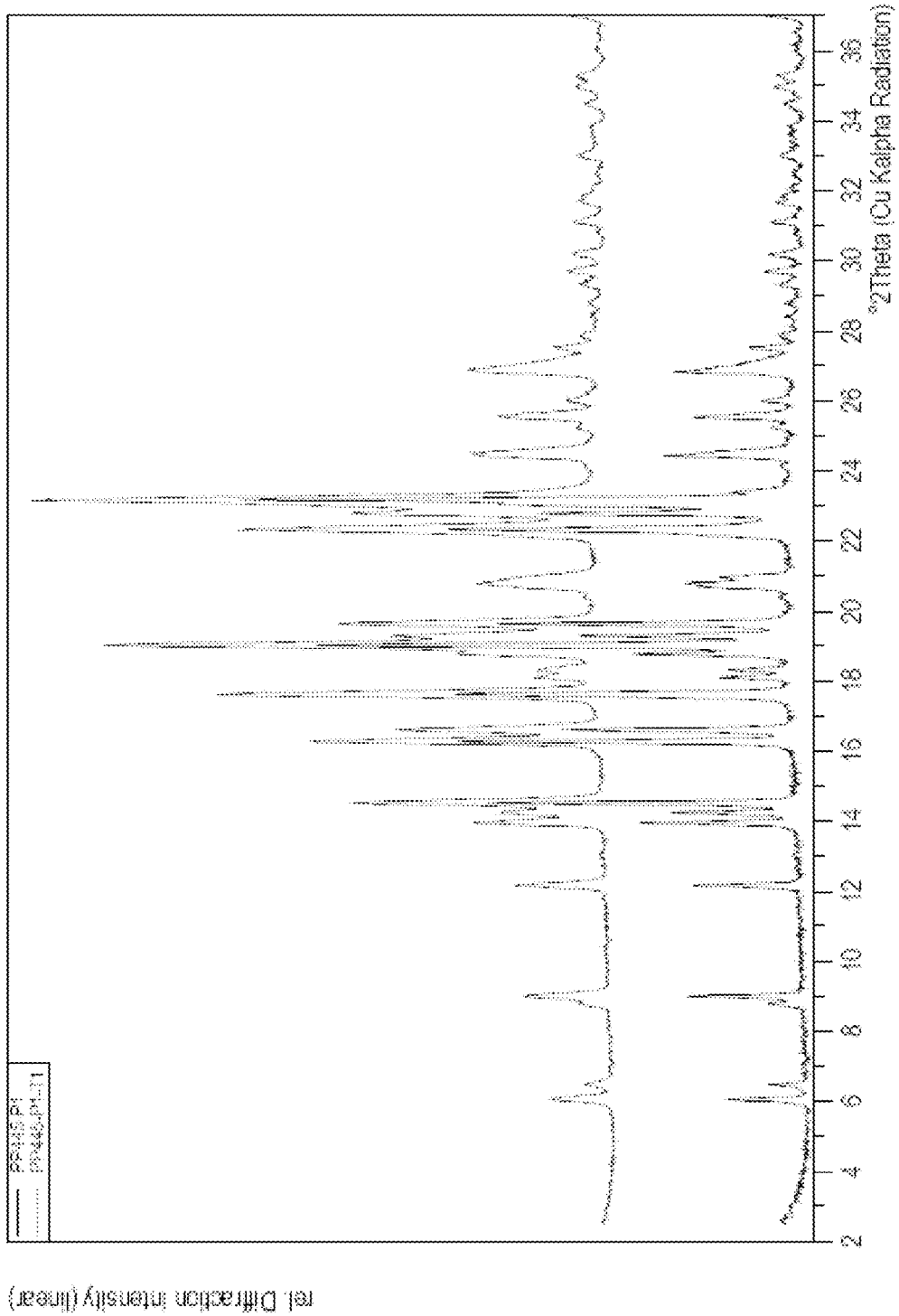
FIG. 8 depicts XRPD patterns of Form B before (top) and after (bottom) drying. The patterns have been scaled and offset in the y-direction for purposes of comparison.

The XRPD pattern of the dried sample (FIG. 8) is unchanged compared to the pattern of the sample before drying.

Figure 9:
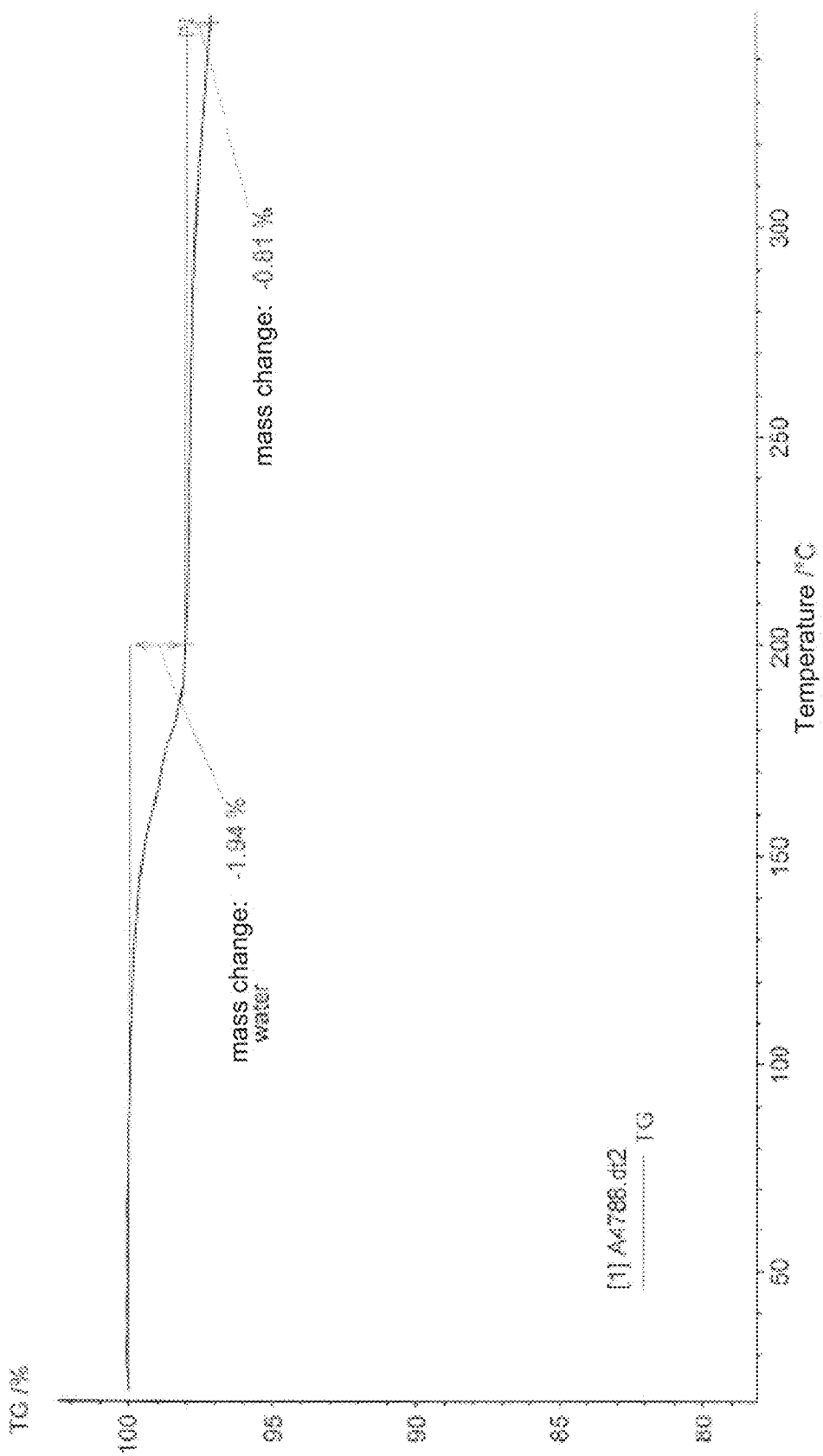
FIG. 9 depicts a TG-FTIR thermogram of a dried sample obtained from Form B.

The TG-FTIR thermogram of the dried sample (FIG. 9) shows the loss of about 1.9 wt % $H_2O$ from 50° C. to 200° C. and decomposition at a temperature greater than about 200. ° C.

Thus, the water seems tightly bound within a stable structure, no dehydration and loss of solvent occurred.

Example 4

Stability Study

A sample of Form B was stored at about 25° C. and about 60% r.h. for a period of time (e.g., 24 months). The concentration of compound 1 in the sample was assayed using HPLC, XRPD, and IR at different time points. The results are shown in Table 7. The term "complies" refers to substantially the same XRPD pattern and/or IR spectrum as the sample at the incept of the storage (time point=initial).

TABLE 7

Stability of Form B stored at about 25° C. and about 60% r.h.

| Time point | Concentration of compound 1 by HPLC Assay (anhydrous basis) | XRPD | IR |
|---|---|---|---|
| Initial | 99.5% w/w | | |
| 3 months | 99.4% w/w | complies | complies |
| 6 months | 99.6% w/w | complies | complies |
| 12 months | 99.3% w/w | complies | complies |
| 18 months | 99.4% w/w | complies | complies |
| 24 months | 99.2% w/w | complies | complies |

The results shown in Table 7 indicate that Form B is stable upon storage for at least 24 months at about 25° C. and about 60% r.h.

Another sample of Form B was stored at about 40° C. and about 75% r.h. for a period of time (e.g., 6 months). The concentration of compound 1 in the sample was assayed using HPLC, XRPD, and IR at different time points. The results are shown in Table 8. The term "complies" refers to substantially the same XRPD pattern and/or IR spectrum as the sample at the incept of the storage (time point=initial).

TABLE 8

Stability of Form B stored at about 40° C. and about 75% r.h.

| Time point | Concentration of compound 1 by HPLC Assay (anhydrous basis) | XRPD | IR |
|---|---|---|---|
| Initial | 99.5% w/w | | |
| 1 month | 99.6% w/w | | |
| 2 months | 99.3% w/w | | |
| 3 months | 99.3% w/w | complies | complies |
| 6 months | 99.4% w/w | complies | complies |

The results shown in Table 8 indicate that Form B is stable upon storage for at least 6 months at about 40° C. and about 75% r.h.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A crystalline Form B of compound 1 of formula:

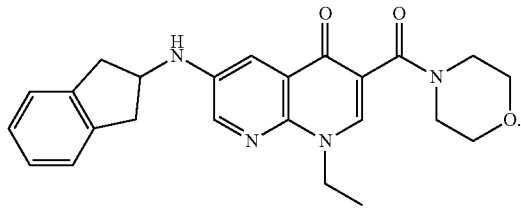

1

2. The crystalline Form B of claim 1, wherein the crystalline Form B is obtained from a mixture of methanol and water.

3. The crystalline Form B of claim 1, wherein the crystalline Form B is a hydrate.

4. The crystalline Form B of claim 1, wherein the crystalline Form B is a hemihydrate.

5. The crystalline Form B of claim 1, wherein the crystalline Form B is a non-stoichiometric hydrate.

6. The crystalline Form B of claim 1, wherein the crystalline Form B is substantially free of amorphous compound 1.

7. The crystalline Form B of claim 1, wherein the crystalline Form B is substantially free of impurities.

8. The crystalline Form B of claim 1, wherein the crystalline Form B is characterized by having four or more peaks in its XRPD pattern selected from those in the following table:

| Angle 2-Theta ° |
| --- |
| 13.94 |
| 14.52 |
| 16.27 |
| 16.60 |
| 17.62 |
| 18.76 |
| 19.02 |
| 19.29 |
| 19.64 |
| 22.32 |
| 22.77 |
| 23.02 |
| 23.16. |

9. The crystalline Form B of claim 1 wherein the crystalline Form B is characterized by having six or more peaks in its XRPD pattern selected from those in the following table:

| Angle 2-Theta ° |
| --- |
| 13.94 |
| 14.52 |
| 16.27 |
| 16.60 |
| 17.62 |
| 18.76 |
| 19.02 |
| 19.29 |
| 19.64 |
| 22.32 |
| 22.77 |
| 23.02 |
| 23.16. |

10. The crystalline Form B of claim 1, wherein the crystalline Form B is characterized by having eight or more peaks in its XRPD pattern selected from those in the following table:

| Angle 2-Theta ° |
| --- |
| 13.94 |
| 14.52 |
| 16.27 |
| 16.60 |
| 17.62 |
| 18.76 |
| 19.02 |
| 19.29 |
| 19.64 |

-continued

| Angle 2-Theta ° |
|---|
| 22.32 |
| 22.77 |
| 23.02 |
| 23.16. |

11. The crystalline Form B of claim 1, wherein the crystalline Form B is characterized by having ten or more peaks in its XRPD pattern selected from those in the following table:

| Angle 2-Theta ° |
|---|
| 13.94 |
| 14.52 |
| 16.27 |
| 16.60 |
| 17.62 |
| 18.76 |
| 19.02 |
| 19.29 |
| 19.64 |
| 22.32 |
| 22.77 |
| 23.02 |
| 23.16. |

12. The crystalline Form B of claim 1, wherein the crystalline Form B is characterized by having all thirteen peaks in its XRPD pattern in the following table:

| Angle 2-Theta ° |
|---|
| 13.94 |
| 14.52 |
| 16.27 |
| 16.60 |
| 17.62 |
| 18.76 |
| 19.02 |
| 19.29 |
| 19.64 |
| 22.32 |
| 22.77 |
| 23.02 |
| 23.16. |

13. The crystalline Form B of claim 1, wherein the crystalline Form B is characterized by having thirty-four peaks in its XRPD pattern selected from those in the following table:

| Angle 2-Theta ° |
|---|
| 6.05 |
| 6.48 |
| 8.78 |
| 9.00 |
| 12.16 |
| 13.94 |
| 14.25 |
| 14.52 |
| 16.27 |
| 16.60 |
| 17.62 |

-continued

| Angle 2-Theta ° |
|---|
| 18.09 |
| 18.31 |
| 18.76 |
| 19.02 |
| 19.29 |
| 19.64 |
| 20.78 |
| 20.95 |
| 22.32 |
| 22.77 |
| 23.02 |
| 23.16 |
| 23.39 |
| 24.42 |
| 25.53 |
| 25.97 |
| 26.82 |
| 27.51 |
| 29.69 |
| 30.17 |
| 31.10 |
| 31.65 |
| 34.96. |

14. The crystalline Form B of claim 1, wherein the crystalline Form B is characterized by a Raman spectrum with at least 11 peaks selected from those in the following table:

| Wavenumber (cm$^{-1}$) |
|---|
| 3322 |
| 3070 |
| 3007 |
| 2993 |
| 2963 |
| 2931 |
| 2910 |
| 2871 |
| 2842 |
| 1636 |
| 1611 |
| 1604 |
| 1508 |
| 1497 |
| 1478 |
| 1459 |
| 1446 |
| 1425 |
| 1393 |
| 1355 |
| 1344 |
| 1319 |
| 1304 |
| 1285 |
| 1271 |
| 1243 |
| 1225 |
| 1208 |
| 1150 |
| 1136 |
| 1112 |
| 1095 |
| 1064 |
| 1039 |
| 1025 |
| 1010 |
| 996 |
| 957 |
| 943 |
| 849 |
| 819 |

-continued

| Wavenumber (cm$^{-1}$) |
|---|
| 810 |
| 789 |
| 741 |
| 713 |
| 681 |
| 603 |
| 585 |
| 555 |
| 501 |
| 484 |
| 446 |
| 419 |
| 372 |
| 349 |
| 316 |

-continued

| Wavenumber (cm$^{-1}$) |
|---|
| 261 |
| 234 |
| 185 |
| 141. |

15. The crystalline Form B of claim 14, wherein the 11 peaks are those in the following table:

| Wavenumber (cm$^{-1}$) |
|---|
| 1636 |
| 1611 |
| 1604 |
| 1446 |
| 1425 |
| 1393 |
| 1355 |
| 1344 |
| 1025 |
| 789 |
| 741. |

16. The crystalline Form B of claim 1, wherein the crystalline Form B is characterized by a DSC thermogram with an endotherm having a peak temperature ($T_{max}$) of about 176° C.

17. The crystalline Form B of claim 1, wherein the crystalline Form B is characterized by a DSC thermogram with a ΔH of about 105 J/g.

18. The crystalline Form B of claim 1, wherein the crystalline Form B is characterized by a glass transition ($T_g$) of about 71° C. after quench cooling.

19. The crystalline Form B of claim 1, wherein the crystalline Form B is characterized by a $\Delta C_p$ of about 0.48 J/(g ° C.) after quench cooling.

20. The crystalline Form B of claim 1, wherein the crystalline Form B is characterized by an IR spectrum with characteristic peaks selected from those in the following table:

| No. | Position | Intensity | No. | Position | Intensity | No. | Position | Intensity |
|---|---|---|---|---|---|---|---|---|
| 1 | 3389.28 | 18.8803 | 2 | 3321.78 | 15.2998 | 3 | 3066.26 | 43.3187 |
| 4 | 3033.48 | 52.327 | 5 | 2991.05 | 44.2454 | 6 | 2970.8 | 36.2048 |
| 7 | 2960.2 | 35.8651 | 8 | 2928.38 | 28.2099 | 9 | 2839.67 | 28.5464 |
| 10 | 2765.42 | 68.3886 | 11 | 2707.57 | 71.199 | 12 | 2684.43 | 72.4374 |
| 13 | 2588.97 | 74.7507 | 14 | 2204.24 | 79.2123 | 15 | 1976.68 | 81.6905 |
| 16 | 1954.5 | 80.4172 | 17 | 1921.72 | 81.2251 | 18 | 1847.47 | 80.7596 |
| 19 | 1807.94 | 79.7842 | 20 | 1680.66 | 59.904 | 21 | 1632.45 | 1.12286 |
| 22 | 1593.88 | 0.229197 | 23 | 1493.6 | 0.785332 | 24 | 1476.24 | 5.24501 |
| 25 | 1458.89 | 16.6916 | 26 | 1431.89 | 12.9634 | 27 | 1390.42 | 25.9737 |
| 28 | 1379.82 | 30.7322 | 29 | 1341.25 | 14.0312 | 30 | 1318.11 | 20.5376 |
| 31 | 1301.72 | 49.2933 | 32 | 1269.9 | 6.91712 | 33 | 1244.83 | 7.5622 |
| 34 | 1216.86 | 21.9545 | 35 | 1209.15 | 26.0253 | 36 | 1128.15 | 55.6498 |
| 37 | 1113.69 | 4.73713 | 38 | 1093.44 | 42.0985 | 39 | 1068.37 | 39.536 |
| 40 | 1036.55 | 51.1775 | 41 | 1023.05 | 68.0011 | 42 | 1005.7 | 62.1369 |
| 43 | 994.125 | 41.5655 | 44 | 955.555 | 72.4243 | 45 | 940.128 | 55.4283 |
| 46 | 905.415 | 77.3957 | 47 | 889.987 | 48.5083 | 48 | 848.525 | 48.9604 |
| 49 | 808.992 | 37.3274 | 50 | 789.707 | 46.8949 | 51 | 754.995 | 16.0235 |
| 52 | 743.424 | 52.7696 | 53 | 710.64 | 66.7717 | 54 | 679.785 | 46.5898 |
| 55 | 601.682 | 34.7989 | 56 | 554.434 | 68.6904 | 57 | 521.65 | 76.6701 |
| 58 | 477.296 | 61.4961 | 59 | 442.583 | 77.4332 | 60 | 428.12 | 78.2972 |
| 61 | 410.763 | 75.3479. | | | | | | |

21. The crystalline Form B of claim 1, wherein the crystalline Form B has an observed melting point of about 155-168° C.

22. The crystalline Form B of claim 1, wherein the crystalline Form B is characterized as having substantially the same XRPD pattern post storage at about 25° C. and about 60% relative humidity for at least 24 months.

23. The crystalline Form B of claim 1, wherein the crystalline Form B is characterized as having substantially the same IR spectrum post storage at about 25° C. and about 60% relative humidity for at least 24 months.

24. The crystalline Form B of claim 1, wherein the crystalline Form B is characterized as having substantially the same XRPD pattern post storage at about 40° C. and about 75% relative humidity for at least 6 months.

25. The crystalline Form B of claim 1, wherein the crystalline Form B is characterized as having substantially the same IR spectrum post storage at about 40° C. and about 75% relative humidity for at least 6 months.

26. A pharmaceutical composition comprising a crystalline Form B of claim 1, and optionally a pharmaceutically acceptable excipient.

27. The pharmaceutical composition of claim 26, wherein the crystalline Form B is in a therapeutically effective amount.

28. A method of treating an anxiety disorder in a subject in need thereof, the method comprising administering to the subject a therapeutically effective amount of a crystalline Form B of claim 1.

29. The method of claim 28, wherein the anxiety disorder is panic disorder, obsessive-compulsive disorder (OCD), post-traumatic stress disorder (PTSD), generalized anxiety disorder (GAD), substance-induced anxiety disorder, acute stress disorder (ASD), irritable bowel syndrome, or fibromyalgia.

30. A method of preparing Form B of claim 1, the method comprising mixing a solution of compound 1 in methanol with an aqueous solution of a base to provide a mixture.

31. The method of claim 30 further comprising lowering the temperature of the mixture to provide a solid.

32. The method of claim 31 further comprising isolating the solid from the mixture.

33. The method of claim 30, wherein the base is selected from $Na_2CO_3$ or $NaHCO_3$.

34. The method of claim 33 wherein the base is $Na_2CO_3$.

35. The method of claim 30, wherein Form B is prepared in greater than 99% purity.

* * * * *